United States Patent [19]
Iwashita et al.

[11] Patent Number: 5,758,649
[45] Date of Patent: Jun. 2, 1998

[54] ULTRASONIC MODULE AND ULTRASONIC DIAGNOSTIC SYSTEM

[75] Inventors: Nobushi Iwashita; Etsuro Machida; Masahiro Hiruta; Kazuhiro Matsumoto; Yoshitaka Abe; Tadahiko Yanashima; Kenichi Hayakawa, all of Kawasaki, Japan

[73] Assignee: Fujitsu Limited, Kawasaki, Japan

[21] Appl. No.: 705,608

[22] Filed: Aug. 30, 1996

[30] Foreign Application Priority Data

Sep. 1, 1995 [JP] Japan ................... 7-225292
Aug. 27, 1996 [JP] Japan ................... 8-225606

[51] Int. Cl.$^6$ ................................. A61B 8/00
[52] U.S. Cl. .................................. 128/662.03
[58] Field of Search ............ 128/660.07, 660.08, 128/661.01, 662.03; 73/625, 626, 628

[56] References Cited

U.S. PATENT DOCUMENTS 5,590,658 1/1997 Chiang et al. ............. 128/661.01

*Primary Examiner*—George Manuel
*Attorney, Agent, or Firm*—Staas & Halsey

[57] ABSTRACT

There is provided an ultrasonic diagnostic system in which an ultrasonic probe is detachably connected thereto, and ultrasonic waves are transmitted from the ultrasonic probe into the subject to obtain received signals through receiving the ultrasonic waves reflected within the subject, thereby displaying for a diagnosis an image carrying information based on the received signals, and is also provided an ultrasonic module including a processing circuit for the received signals, the ultrasonic module being used in the ultrasonic diagnostic system. The diagnotics system and the diagnostic module according to the present invention permit the more extensive patients to have an ultrasonic diagnosis, and also permit the operator to have a higher level of computer support. The ultrasonic module is connected through a general-purpose interface to a computer system. An ultrasonic module, which has, as a main element, an analog unit for performing an analog signal processing, is connected to another computer system.

38 Claims, 15 Drawing Sheets

ULTRASONIC MODULE AND ULTRASONIC DIAGNOSTIC SYSTEM

BACKGROUND OF THE INVENTION

1. Field of the Invention

The present invention relates to an ultrasonic diagnostic system in which an ultrasonic probe is detachably connected thereto, and ultrasonic waves are transmitted from the ultrasonic probe into the subject to obtain received signals through receiving the ultrasonic waves reflected within the subject, thereby displaying for a diagnosis an image carrying information based on the received signals, and also relates to an ultrasonic module including a processing circuit for the received signals, the ultrasonic module being used in the ultrasonic diagnostic system.

2. Description of the Related Art

Hitherto, there has been widely used an ultrasonic diagnostic apparatus including the above-mentioned ultrasonic diagnostic system, utilizing the features such as a safety for a living body, a non-invasion and a visualization of the soft tissue, in the field of diagnoses in the medical treatment particularly for a cardiac and the abdomen.

FIG. 17 is a block diagram showing the basic arrangement of constituents of an ultrasonic diagnostic apparatus in accordance with the related art.

Detachably connected to the ultrasonic diagnostic apparatus 10 is an ultrasonic probe 20 and an information output device 30 which comprises a video cassette recorder (VCR) (video tape recorder: VTR) 31 for recording thereon images, a printer 32 for outputting information on a sheet, and a monitor 33 for displaying images on a display screen.

The ultrasonic probe 20 is put to a patient 1 and sequentially transmits ultrasonic pulse beams in directions along scan lines 2 extending to the inside of the patient 1, and also generates electric signals upon picking up ultrasonic waves reflecting inside of the patient 1. The ultrasonic probe 20 is connected through a probe loading unit 110 to an analog section 120 which serves to process analog signals except for control signals and an output of an A/D converter of the final stage. The analog section 120 comprises: a beam scan control unit 121 for performing a control of a transmission of the ultrasonic pulse beams as to the directions along the scan lines 2 inside of the patient 1; a transmission and receiving delay control unit 122 responsive to an instruction signal generated by the beam scan control unit 121 for controlling a drive circuit 123 and a beamformer 125; the drive circuit 123 for driving the ultrasonic probe 20 under the control of the transmission and receiving delay control unit 122 in such a manner that the ultrasonic pulse beam is transmitted in a direction along a predetermined scan 2; a receiving circuit 124 for receiving signals picked up by the ultrasonic probe 2; a beamformer 125 for beamforming the received signals so as to emphasize information as to the direction along a predetermined scan 2 inside of the patient 1 in accordance with the received signals generated by the receiving circuit 124; an analog signal processing 126 for applying an analog processing comprising, for example, a detection processing, a filtering processing and the like, to the received signals after the beamforming outputted from the beamformer 125, and an A/D converter 127 for converting the analog signals outputted from the analog signal processing 126 into digital signals.

The signals outputted from the analog section 120 are sent to a digital section 130. The digital section 130 comprises: a scan converter 131 for converting the signals received from the analog section 120 into raster signals for use in image outputting; and a digital image processing unit 132 for applying a digital processing, for example, a frequency emphasis processing, a gray level transformation processing and the like, to the signals outputted from the scan converter 131.

Incidentally, a distinction of the analog section and the digital section is made for the sake of convenience. In some cases, the detection and the filtering are of the digital processing.

The signals outputted from the digital section 130 are sent to a display section 140. The display section 140 serves to display on a display screen of the monitor 33 the signals entered from the digital section 130 and the signals entered from the video cassette recorder (VCR) 31, and also serves to perform a processing for supplying information based on the signals outputted from the digital section 130 to the VCR 31 and the printer 32. Specifically, the display section 140 comprises: a TV signal generator 141 for generating a TV signal; an output device control unit 142 for controlling the information output device 30; a freeze memory 143 for storing signals involved in a specific image frame of the signals entered from the digital section 130 to form a still picture; a video D/A converter unit 144 for converting output signals directed to the VCR 31 into analog signals and for converting input signals received through the VCR 31 into digital signals; an imposing unit 145 for superimposing an image entered from the VCR 31 on an image entered from the digital section 130 and also for superimposing characters on the resultant image, so that an image to be displayed on the monitor is formed; and a signal conversion unit 146 for converting the signals entered from the digital section 130 and the signals entered from the VCR 31 into NTSC signals and PAL signals which are of a form suitable for the monitor 33.

A system control unit 150 serves to control the ultrasonic diagnostic apparatus 10 in its entirety, that is, the analog section 120, the digital section 130 and the display section 140.

An operation panel 160 comprises an operation key, a track ball, a monitor lamp and the like. Through operating the operation panel 160, there is inputted a control specification as to a control of the ultrasonic diagnostic apparatus 10 in its entirety to the system control unit 150.

To practice a diagnosis for patient 1 with the use of the ultrasonic diagnostic apparatus 10 constructed as mentioned above, the ultrasonic probe 20 is put on a body surface of the affected part of patient 1, and the operation panel 160 is operated so that ultrasonic waves are transmitted inside of the body of the patient 1 and reflected ultrasonic waves are received to obtain received signals. An analog processing and a digital processing are applied to the received signals thus obtained, and then displayed on the monitor 33. Alternatively, the processed received signals are recorded first on the VCR 31 and thereafter displayed on the monitor 33 so as to practice the diagnosis while observing the associated image displayed on the monitor 33.

According to an ultrasonic diagnostic system using the conventional ultrasonic diagnostic apparatus, an operator (doctors or technicians) performs examination and diagnosis in an examination room or a hospital ward. Details of the examination and diagnosis will be classified in the performance as follows.

First, in case of the doctor, there are two cases in one of which the operator performs a diagnosis while directly observing an examination screen displayed on the monitor 33, and the ultrasonic image corresponding to the diagnosis and the associated information are recorded on the VCR 31 and printed by the printer 32. In another case, the ultrasonic images necessary for a diagnosis are recorded on the VCR 31 for each patient, and after examinations, the doctor gives a decision for the diagnosis while reproducing the recorded images.

On the other hand, in case of the technicians, the required ultrasonic images are recorded on the VCR 31 for each patient, and then the video tapes or the like, on which the ultrasonic images are recorded, are transferred to a doctor. The doctor gives a decision for the diagnosis while reproducing the recorded images.

Thus, it is necessary for a patient, who wishes to have a diagnosis, to go to a hospital which is equipped with an ultrasonic diagnostic apparatus, and in which there is a doctor who can interpret the ultrasonic images.

By the way, recently, in the field of information processings using particularly computers as the main part, the technical idea of the downsizing permeates, so that a centralized network system in which the satellite computers and/or the terminal equipments are connected to a large scale computer in the form of a core is going to be replaced by a distributed network system in which workstation/personal computer are connected to each other through a LAN or a communication network. A standardization of an OS (Operating System) or an opening of an architecture brings about various application softwares. Thus, the computer is about to be a tool which is necessary for an individual. On the other hand, in the field of communications, taking into account the next century, there has been developed a network construction capable of transmitting and receiving any kinds of media such as computers, videos and audio in the bi-direction.

SUMMARY OF THE INVENTION

In view of the foregoing, it is therefore an object of the present invention to provide an ultrasonic diagnostic system suitable for the above-mentioned social environment; through which ultrasonic diagnostic system more extensive patients have the ultrasonic diagnosis, and an ultrasonic module used in the ultrasonic diagnostic system.

To achieve the above-mentioned objects, according to the present invention, there is provided the first ultrasonic module comprising: an analog unit for supplying drive signals for a transmission of ultrasonic waves to an ultrasonic probe adapted for transmitting and receiving ultrasonic waves, and for practicing an analog signal processing on received signals obtained through said ultrasonic probe; a digital unit for practicing a digital signal processing on signals generated from said analog unit; a display circuit unit for practicing a processing for causing an image display to display an image based on signals generated from said digital unit; a system control unit for controlling said analog unit, said digital unit and said display circuit unit; an operation panel unit for inputting an instruction as to a control specification to said system control unit; an input unit for inputting a control specification issued from an exterior to said system control unit; and an output unit for outputting the signals generated from said digital unit to an exterior, wherein all of said units are incorporated in one united body.

To achieve the above-mentioned objects, according to the present invention, there is provided the second ultrasonic module comprising: an analog unit for supplying drive signals for a transmission of ultrasonic waves to an ultrasonic probe adapted for transmitting and receiving ultrasonic waves, and for practicing an analog signal processing on received signals obtained through said ultrasonic probe; a digital unit for practicing a digital signal processing on signals generated from said analog unit; a display circuit unit for practicing a processing for causing an image display to display an image based on signals generated from said digital unit; a system control unit for controlling said analog unit, said digital unit and said display circuit unit; an input unit for inputting a control specification issued from an exterior to said system control unit; and an output unit for outputting the signals generated from said digital unit to an exterior, wherein all of said units are incorporated in one united body.

To achieve the above-mentioned objects, according to the present invention, there is provided the third ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; a system control unit for controlling said analog unit; and an output unit for outputting signals generated from said analog unit to an exterior, wherein all of said units are incorporated in one united body.

To achieve the above-mentioned objects, according to the present invention, there is provided the fourth ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; an input unit for inputting a control signal to control said analog unit; and an output unit for outputting signals generated from said analog unit to an exterior, wherein all of said units are incorporated in one united body.

To achieve the above-mentioned objects, according to the present invention, there is provided the first ultrasonic diagnostic system comprising:

an ultrasonic module comprising: an analog unit for supplying drive signals for a transmission of ultrasonic waves to an ultrasonic probe adapted for transmitting and receiving ultrasonic waves, and for practicing an analog signal processing on received signals obtained through said ultrasonic probe; a digital unit for practicing a digital signal processing on signals generated from said analog unit; a display circuit unit for practicing a processing for causing an image display to display an image based on signals generated from said digital unit; a system control unit for controlling said analog unit, said digital unit and said display circuit unit; an operation panel unit for inputting an instruction as to a control specification to said system control unit; an input unit for inputting a control specification issued from an exterior to said system control unit; and an output unit for outputting the signals generated from said digital unit to an exterior, wherein all of said units are incorporated in one united body; and a computer system connected to said input unit and said output unit of said ultrasonic module, said computer system being capable of performing an output of a control specification for controlling said ultrasonic module, a filing of information based on signals generated from said output unit, and a display of images based on the signals generated from said output unit.

To achieve the above-mentioned objects, according to the present invention, there is provided the second ultrasonic diagnostic system comprising:

an ultrasonic module comprising: an analog unit for supplying drive signals for a transmission of ultrasonic waves to an ultrasonic probe adapted for transmitting and receiving ultrasonic waves, and for practicing an analog signal processing on received signals obtained through said ultrasonic probe; a digital unit for practicing a digital signal processing on signals generated from said analog unit; a display circuit unit for practicing a processing for causing an image display to display an image based on signals generated from said digital unit; a system control unit for controlling said analog unit, said digital unit and said display circuit unit; an input unit for inputting a control specification issued from an exterior to said system control unit; and an output unit for outputting the signals generated from said digital unit to an exterior, wherein all of said units are incorporated in one united body;

an operation panel in which incorporated thereinto are an operation panel unit for inputting an instruction as to a control specification for a control of said analog unit, said digital unit and said display circuit unit in said system control unit, and an additional output unit for outputting the control specification produced through an operation by said operation panel unit to an exterior; and a computer system connected to said input unit and said output unit of said ultrasonic module, and also to said additional output unit of said operation panel, said computer system being capable of performing an output of a control signal for controlling said ultrasonic module generated based on the control specification entered through said operation panel, a filing of information based on signals generated from said output unit, and a display of images based on the signals generated from said output unit.

To achieve the above-mentioned objects, according to the present invention, there is provided the third ultrasonic diagnostic system comprising:

an ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; a system control unit for controlling said analog unit; and an output unit for outputting signals generated from said analog unit to an exterior, wherein all of said units are incorporated in one united body; and a computer system connected to said output unit of said ultrasonic module, said computer system being capable of performing a digital signal processing to be practiced on signals generated from said ultrasonic module, a filing of information based on signals subjected to the digital signal processing, and a display of images based on the signals subjected to the digital signal processing.

To achieve the above-mentioned objects, according to the present invention, there is provided the fourth ultrasonic diagnostic system comprising:

an ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; an input unit for inputting a control signal to control said analog unit; and an output unit for outputting signals generated from said analog unit to an exterior, wherein all of said units are incorporated in one united body; and a computer system connected to said input unit and said output unit of said ultrasonic module, said computer system being capable of performing an output of a control signal for controlling said ultrasonic module, a digital signal processing to be practiced on signals generated from said ultrasonic module, a filing of information based on signals subjected to the digital signal processing, and a display of images based on the signals subjected to the digital signal processing.

In the first to fourth ultrasonic diagnostic systems, it is preferable that said computer system comprises: diagnostic file producing means for producing a diagnostic file, on each diagnosis for each patient, containing at least patient ID information for discriminating patients, one or more sheets of image produced on the basis of signals generated from said ultrasonic module, and image collection conditions representative of a state of said ultrasonic module involved in a time when the signals, on the basis of which the images are produced, are obtained in said ultrasonic module; and editing means for extracting and collecting information based on a designated editing specification from among a plurality of diagnostic files produced by said diagnostic file producing means.

In this case, it is preferable that said computer system comprises: electronic clinical record producing means for producing an electronic clinical record containing one's view as to said diagnostic file, an image extracted from said diagnostic file, and a line drawing image produced on the basis of the image extracted from said diagnostic file.

It is also preferable that said computer system comprises: diagnostic condition setting means for transmitting, at a time of a re-examination to again obtain signals for producing images, using said ultrasonic module, on a patient specified by the patient ID recorded in anyone of the diagnostic files produced at the past, image collection conditions recorded on the diagnostic file produced at the past on the same patient to said ultrasonic module.

Further, it is also preferable that said computer system comprises: image display means for displaying, at a time of a re-examination to again obtain signals for producing images, using said ultrasonic module, on a patient specified by the patient ID recorded in anyone of the diagnostic files produced at the past, image recorded on the diagnostic file produced at the past on the same patient.

In the first to fourth ultrasonic diagnostic systems, it is preferable that said computer system comprises: navigation image display means for displaying a navigation image to support an operation for deriving images using said ultrasonic module.

To achieve the above-mentioned objects, according to the present invention, there is provided the fifth ultrasonic diagnostic system comprising:

an ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; a system control unit for controlling said analog unit; and an output unit for outputting signals generated from said analog unit to an exterior, wherein all of said units are incorporated in one united body;

a second computer system connected to said output unit of said ultrasonic module, said computer system being capable of performing a data communication, via a communication line, including a transmission of signals outputted from said ultrasonic module; and a first computer system connected via said communication line to said second computer system, said first computer system being capable of performing a data communication including a reception of the signals outputted from said ultrasonic module and transmitted from said second computer system, and also being capable of producing images based on received signals.

To achieve the above-mentioned objects, according to the present invention, there is provided the sixth ultrasonic diagnostic system comprising:

an ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; an input unit for inputting a control signal to control said analog unit; and an output unit for outputting signals generated from said analog unit to an exterior, wherein all of said units are incorporated in one united body;

a second computer system connected to said input unit and said output unit of said ultrasonic module, said second computer system being capable of performing a transmission of a control signal for controlling said ultrasonic module to said ultrasonic module, and also being capable of performing a data communication, via a communication line, including a transmission of signals outputted from said ultrasonic module; and a first computer system connected via said communication line to said first computer system, said first computer system being capable of performing a data communication including a reception of the signals outputted from said ultrasonic module and transmitted from said second computer system, and also being capable of producing images based on received signals.

In the fifth to sixth ultrasonic diagnostic system, it is preferable that said first computer system comprises:

transmitting means for transmitting to said second computer system a signal representative of a navigation image to support an operation for deriving images using said ultrasonic module, and that said second computer system comprises:

receiving means for receiving the signal representative of the navigation image transmitted from said first computer system; and navigation image display means for displaying the navigation image based on received signals.

In the fifth to sixth ultrasonic diagnostic system, it is preferable that said ultrasonic diagnostic system comprises an ultrasonic probe device having an ultrasonic probe for transmitting and receiving ultrasonic waves, a pointing device for designating a position on a screen, and a cable for carrying a transmission of signals transferred between said ultrasonic probe and said pointing device and said ultrasonic module.

In the fifth to sixth ultrasonic diagnostic system, it is preferable that said ultrasonic diagnostic system comprises an ultrasonic probe device having an ultrasonic probe for transmitting and receiving ultrasonic waves, a pointing device for designating a position on a screen, a first cable for carrying a transmission of signals transferred between said ultrasonic probe and said ultrasonic module, and a second cable for carrying a transmission of signals transferred between said pointing device and said first computer system.

Incidentally, as mentioned above, a distinction of the analog section and digital section is made for the sake of convenience. It is acceptable that the detection and the filtering explained in the related art are of the digital processing. Consequently, the analog section referred to in the present invention implies a broad concept including a minimum structure comprising only an amplification (including suppression).

DESCRIPTION OF THE PREFERRED EMBODIMENTS

Hereinafter, there will be described embodiments of the present invention.

Figure 1:
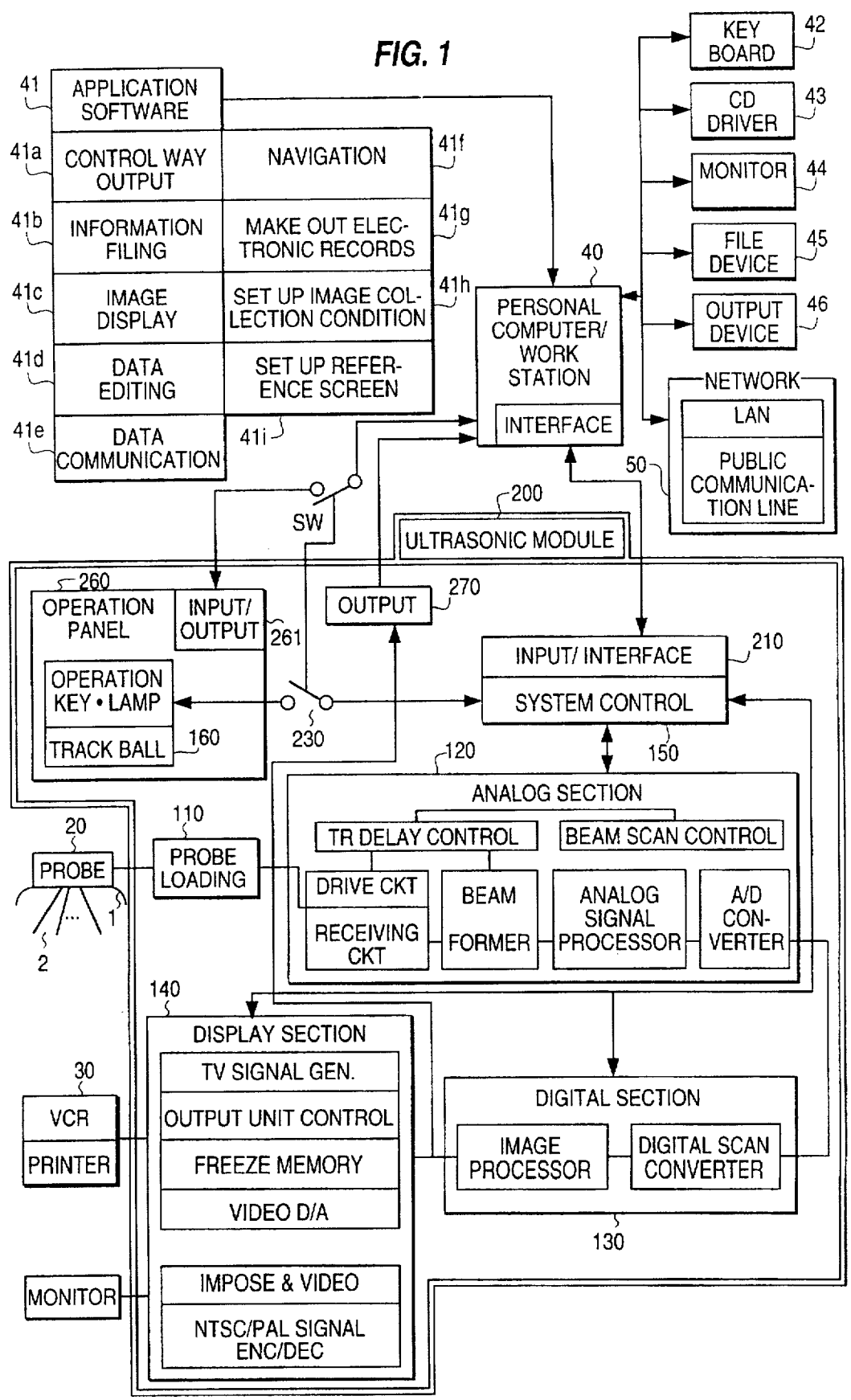
FIG. 1 is a functional block diagram of a first ultrasonic module and a first ultrasonic diagnostic system according to the first embodiment of the present invention.

FIG. 1 is a functional block diagram of a first ultrasonic module and a first ultrasonic diagnostic system according to the first embodiment of the present invention. In FIG. 1, the same parts are denoted by the same reference numbers as those of FIG. 17. And the redundant description will be omitted.

Figure 17:
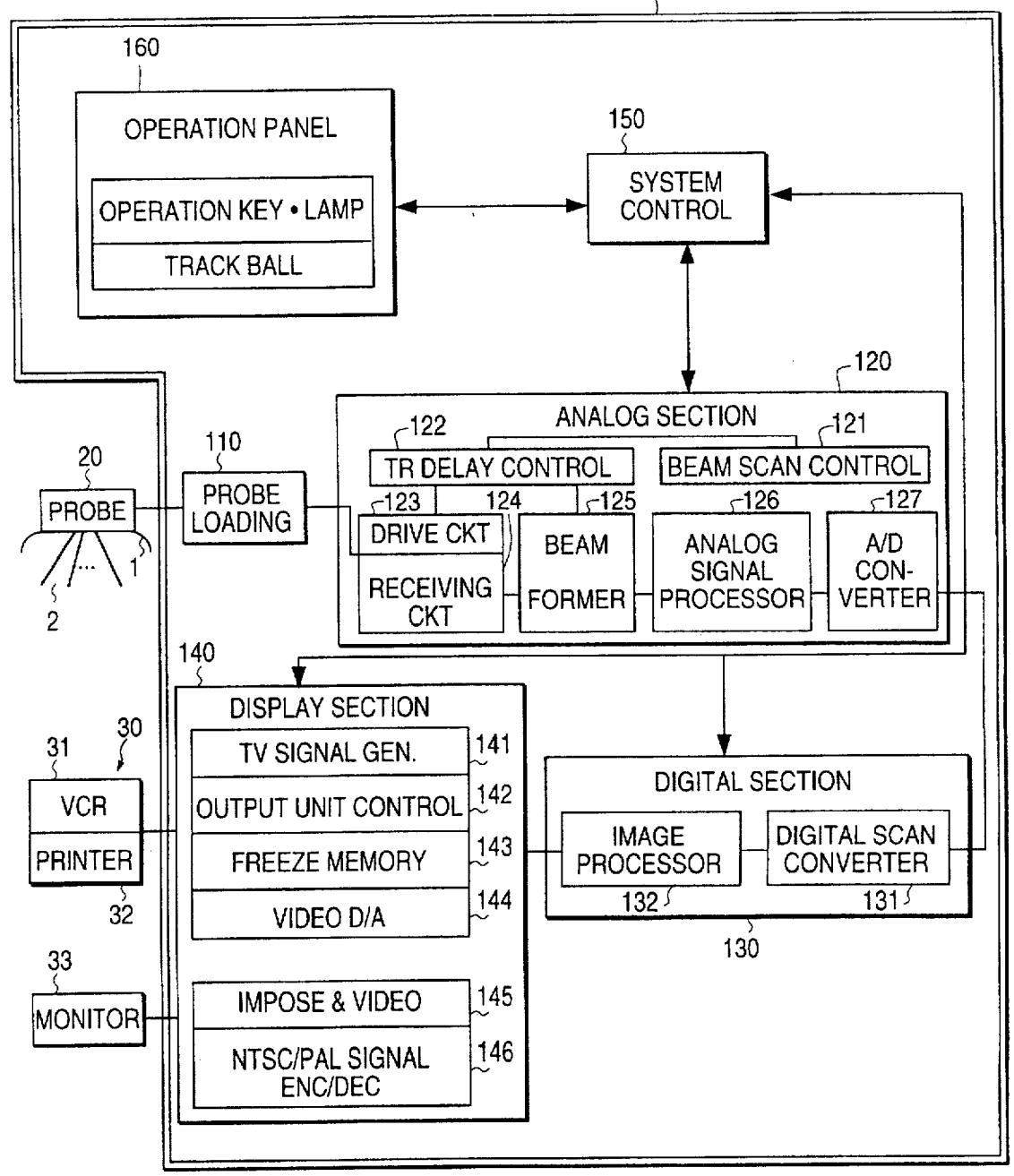
FIG. 17 is a block diagram showing the basic arrangement of constituents of an ultrasonic diagnostic apparatus in accordance with the related art.

An ultrasonic module 200 shown in FIG. 1 comprises, similar to the ultrasonic diagnostic apparatus shown in FIG. 17 in the structure, a probe loading unit 110, an analog section 120, a digital section 130, a display section 140, a system control unit 150 and an operation panel unit 160. An operation panel 260 including the operation panel unit 160 has an input/output unit 261 comprising an output section for outputting a signal representative of the operation content of the operation panel unit 160 to a general-purpose computer system such as a personal computer and a workstation, and an input section for receiving a signal to control turn-on and turn-off of a monitor lamp of the operation panel unit 160.

When the operation panel unit 160 of the operation panel 260 is operated, the operation content is sent via a selection switch 230 to the system control unit 150. Alternatively, the operation content is sent to the computer system 40 and then sent via the computer system 40 to the ultrasonic module 200. The operation content is sent, when passing through the computer system 40, via an input section 210 having a general-purpose interface, for example, an RS232C interface, to the system control unit 150.

The ultrasonic module 200 further comprises an output unit 220 for outputting the signals generated from the digital unit 130 toward the computer system 40. While FIG. 1 depicts individually the input section 210 constituting the ultrasonic module 200, the output unit 220, and the input/output unit 261 constituting the operation panel 260 in the ultrasonic module 200, it is acceptable that those items are constituted of a single interface physically.

The computer system 40 comprises: a keyboard 42 for entering character data to the computer system 40; a CD (compact disk) driver 43, on which a CD is mounted, adapted to load the program and data stored in the CD into the computer system 40; a monitor device 44 for displaying images; a filing device 45 for preserving data in, for example, a hard disk, a floppy disk and an MO; and an output device 46 for producing a hard copy of information, such as a printer having, for example, a centronics interface or IEEE 1284 interface. The computer system 40 is connected also to a network 50 such as a LAN and a public communication line (telephone line), so that data are transmitted via the network 50. An application software 41 suitable for the ultrasonic diagnostic system is loaded into the computer system 40 from the CD mounted on, for example, the CD driver 43. Of the application software 41 the main ones are: a control specification output routine 41a for outputting, when the operation content of the operation panel 260 is entered via the selection switch 230, a control specification representative of the operation content in its or in the rm or in the modified form to the ultrasonic module 200; an information filing routine 41b responsive to a signal generated from the output unit 220 of the ultrasonic module 200 for filing information based on the received signal into the filing device 45; an image display routine 41c for displaying an image based on the received signal on a display screen of the monitor device 44; a data editing routine 41d for editing data filed into the filing device 45; a data communication routine 41e for transmitting through the network 50 data entered from the ultrasonic module 200 and data read out from the filing device 45 and for receiving data via the network 50; a navigation routine 41f for instructing the image display routine 41c to display on the display screen of the monitor device 44 a navigation image to support an operation such that the ultrasonic probe 20 is put on a surface of the body of the patient 1 to obtain images through transmitting and receiving ultrasonic waves; an electronic clinical record making routine 41g for making an electronic clinical record in the format of report when one's view as to a diagnosis result on the patient by a doctor or the like is inputted; an image collection condition setting routine 41h for setting up the ultrasonic module 200 to the image collection condition in such a manner that when the diagnosis on the same patient is performed again, the image collection condition, which is representative of the condition of the ultrasonic module 200 involved in the past when the ultrasonic images were collected on the patient using the ultrasonic module 200, for example, a gain of the receiving circuit, a constant of the filter in the analog signal processing, and the like, is transmitted to the ultrasonic module 200; and a reference screen setting routine 41i for causing the image display routine 41c to display on a display screen of the monitor device 44, when the diagnosis on the same patient is performed again, the image (reference image) collected in the past on the same patient for the purpose of comparison with the image now collected.

Figure 2:
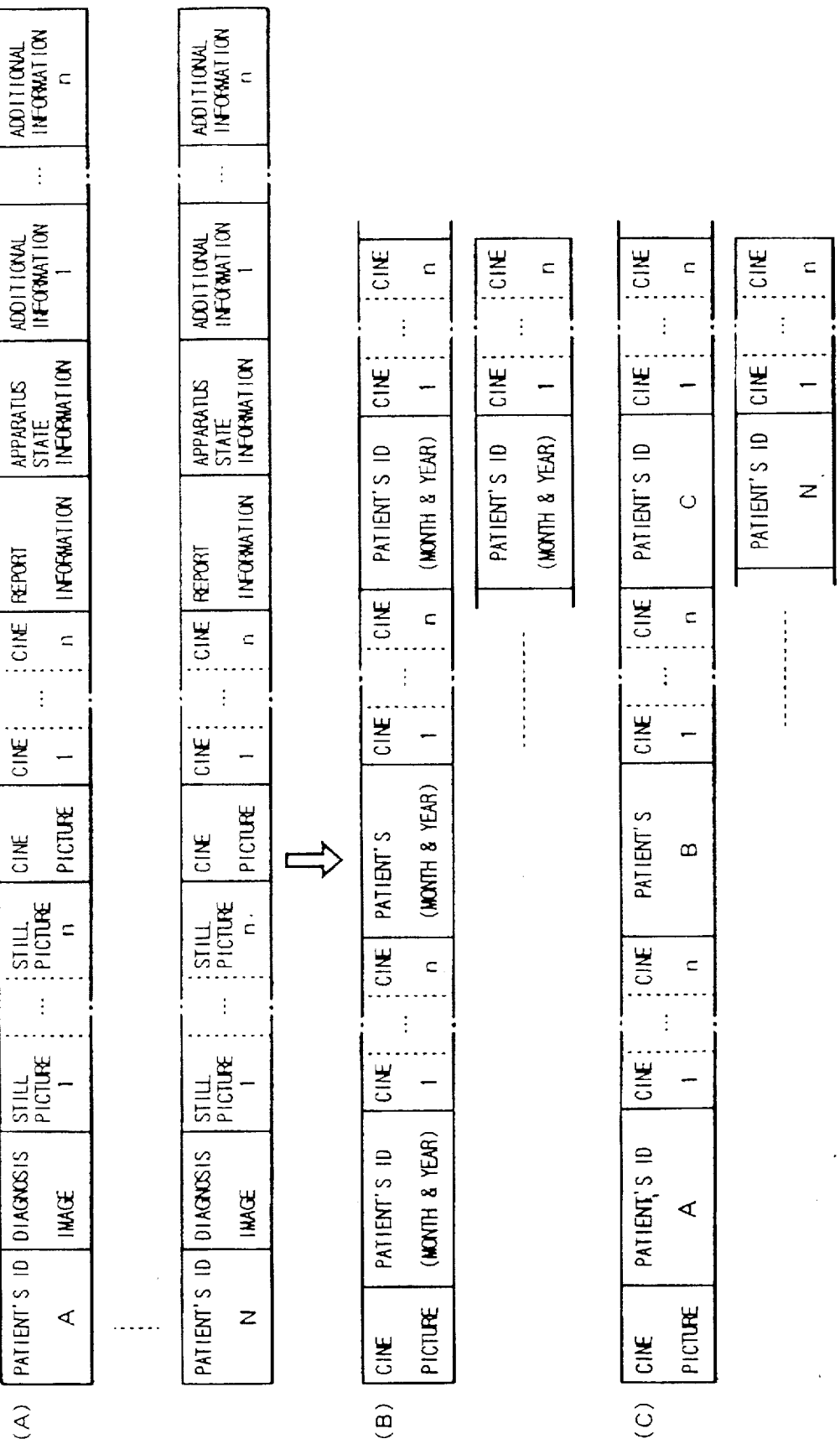
FIG. 2 is a functional explanatory view useful for understanding an information filing routine and a data edit routine in the computer system shown in FIG. 1.

FIG. 2 is a functional explanatory view useful for understanding the information filing routine 41b and the data edit routine 41d in the computer system 40 shown in FIG. 1.

The probe 20 is put on a surface of the body of the patient. Whenever a "one time" diagnosis is performed, the information filing routine 41b is actuated, so that a diagnosis file having a format shown in part (A) of FIG. 2 is made and stored in, the filing device 45 of the computer system 40. Recorded in each diagnosis file are a patient's ID for identifying the patient; a diagnosis image consisting of a plurality of still pictures 1–n; a plurality of cine pictures (animation) 1–n; report information (electronic clinical records) recording therein a doctor's view on the diagnosis through his observation of those images or pictures; apparatus state information representative of states of the ultrasonic module 200, the computer system 40 and other peripheral equipments, including the image collection conditions representative of the state of the ultrasonic module 200 involved in the time when those images are obtained; and additional information, for example, messages as to diagnostic time and day, a case history of the patient, a progress situation of the disease which the patient now suffers from; and the patient's constitution.

The filing device 45 stores, as shown in part (A) of FIG. 2, a lot of diagnostic files made out for each diagnosis of each patient.

Part (B) of FIG. 2 shows an example of a personal diagnosis history file in which of a lot of diagnostic files shown in part (A) of FIG. 2 only the cine images of the specified patients are edited. Part (C) of FIG. 2 shows an example of a similar case editing file in which of a lot of diagnostic files shown in part (A) of FIG. 2 only the cine images of the patients having the similar cases are edited.

The data editing routine 41d is responsive to an operation by an operator for making out the personal diagnostic history file and the similar case editing file as shown in parts (B) and (C) of FIG. 2, respectively, on the basis of a lot of diagnostic files of the type as shown in part (A) of FIG. 2.

Preparation of the editing function as mentioned above may contribute to an effective utilization of data on a lot of patients obtained once. Particularly, regarding the personal diagnostic history file, it is possible to observe a change with elapse in the condition of a disease of the patient, thereby practicing the better treatment suitable for the patient. Regarding the similar case editing file, re-editing through setting up sex, age, weight, height and other condition may provide such a possibility that information effective in diagnosis is derived.

Figure 3:
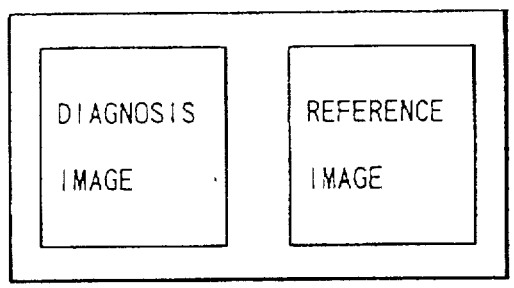
FIG. 3 is an illustration showing a display screen of a monitor device in the computer system shown in FIG. 1 in a state that a probe is put on a surface of the body of a patient to collect image signals.

FIG. 3 is an illustration showing a display screen of a monitor device 44 in the computer system 40 shown in FIG. 1 in a state that a probe 20 is put on a surface of the body of patient 1 to collect image signals.

In a case where a patient, on whom image signals are intended to be collected now, is of the first coming, the reference image is not displayed. In this case, a doctor or a technician, who has an ability of operating the ultrasonic diagnostic system, takes in the ultrasonic images (diagnosis image) of the patient in accordance with the regular operation, while adjusting the image collection conditions such as the gain and the filter parameter to the optimum value for the patient. When taking in of the image as to the one time diagnosis is terminated, as mentioned above, the information filing routine 41b is actuated to make out the diagnostic file in which apparatus state information including the image collection condition at that time is stored (cf. part (A) of FIG. 2).

In a case where a patient, on whom image signals are intended to be collected now, is of re-diagnosis, the diagnostic file, which was previously made out on the same patient, is read out and the image collection condition setting routine 41h is actuated, so that the image collection conditions involved in the previous image collection are sent out to the ultrasonic module 200, whereby the gain, the filter parameter and the like are automatically adjusted to meet the image collection conditions. This makes it possible to extremely ease the troublesomeness in an operation by the doctor and the engineer, thereby expecting an efficient image collection.

In collection of images, the reference screen setting routine 41i is actuated, as shown in FIG. 3, so that the diagnostic image in the diagnostic file previously made out on the same patient is displayed in the form of a reference image, on the display screen of the monitor device 44, together with the diagnostic image now on collection. This makes it possible for a doctor or a technician to obtain the diagnostic image having a tomographic plane near that of the past diagnostic image (reference image), thereby making it easy to compare those images with one another. Thus, it is possible to observe a change with elapse, whereby the doctor easily grasp a progressing situation of a disease of the patient.

Figure 4:
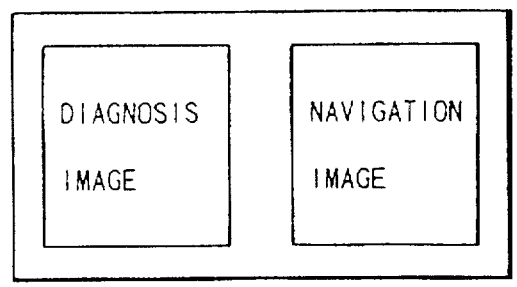
FIG. 4 is an illustration showing a display screen of a monitor device in the computer system shown in FIG. 1 in a state that images are going to be collected or has been collected from a patient.

FIG. 4 is an illustration showing a display screen of a monitor device 44 in the computer system 40 shown in FIG. 1 in a state that images are going to be collected or has been collected from a patient.

When the navigation routine 41f is actuated, displayed in a part of the navigation image on the display screen of the monitor device 44 are an operation guide of the ultrasonic diagnostic system; a standard operational procedure of the probe 20; and a typical cine image, a previous collected cine image (navigation image) which will be obtained when the operation is made in accordance with the standard operational procedure. When the navigation image is displayed, the navigation image is stored in a RAM (not illustrated), and is reproduced at a time interval (time scale) which is the same as the actual diagnostic image.

In this manner, it is possible to provide a substantially complete support in a treatment of the ultrasonic diagnostic system for a doctor or a technician who are unaccustomed to the treatment of the ultrasonic diagnostic system.

Figure 5:
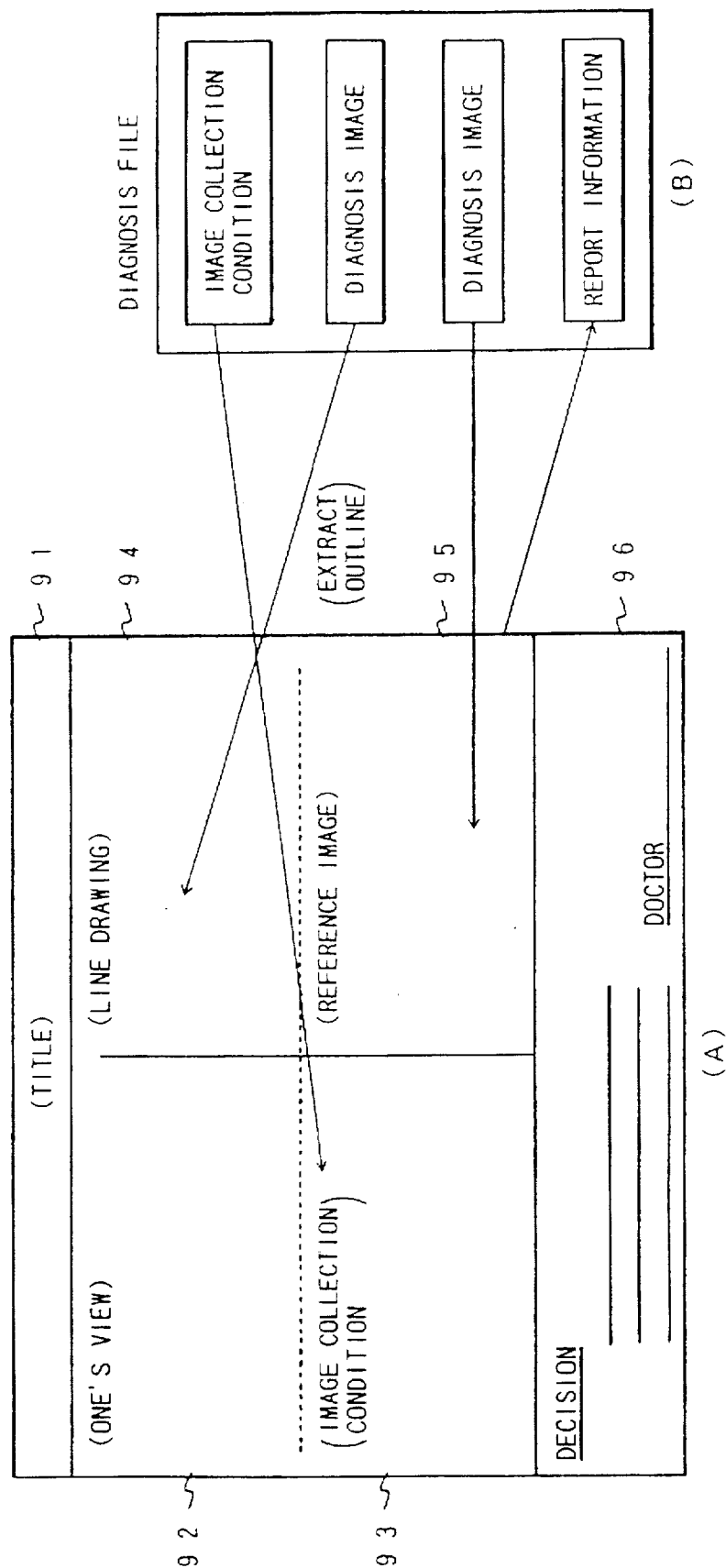
FIG. 5 is an illustration showing an electronic clinical record format by way of example.

FIG. 5 is an illustration showing an electronic clinical record format by way of example.

When images on one time of diagnosis are collected from a patient, the electronic clinical record making routine 41g is actuated, so that an electronic clinical record format as shown in part (A) of FIG. 5 is displayed on the display screen of the monitor device 44. An electronic clinical record on the patient is made out and stored in the diagnosis file in the form of report information (cf. part (A) of FIG. 2).

The electronic clinical record format is partitioned into a title column 91 in which messages specifying a patient name, a disease name, a diagnosis date and the like are described; a view column 92 in which a doctor's view is described in the form of a document through an operation by the keyboard 42; an entry column 93 for image collection conditions involved in the image collection, the image collection conditions being recorded in the diagnosis file; a display column 94 for a line drawing simulating the ultrasonic image; a display column 95 for a reference image consisting of one or a plurality of ones of the diagnostic images; and an entry column 96 for an overall decision by a doctor. In the display column 94 for a line drawing, there is displayed a line drawing image produced by means of outline extracting on the basis of a suitable diagnostic image in the diagnostic file. In the display column 95 for a reference image, there are displayed one or a plurality of diagnostic images which most clearly show the condition of a patient.

Messages such as the patient's ID and image collection date, which are recorded in the diagnostic file, are automatically transferred from the diagnostic file to the title column 91 by the electronic clinical record making routine 41g. Other messages are entered by doctors or the like. In the view column 92, a doctor's view is described, and at that time, if necessary, a mark indicating where symptoms appears is appended on the line drawing image.

When making out of the electronic clinical record is terminated, the electronic clinical record is stored in the column of the report information in the diagnostic file. Thus, a completed diagnostic file is formed.

Regarding making out of the electronic clinical record, hitherto, there is an example in which a line drawing image is made out individually and displayed on an illustration basis independent of the actual diagnostic image. On the contrary, according to the present invention, a line drawing image is made out by means of an outline extraction and the like on the basis of the actual diagnostic image, and then displayed on the display column 94 for a line drawing. This feature makes it easy to designate a position on which disease symptoms appears and also to confirm the disease symptoms after day. Particularly, it may become a useful information in case of the progress diagnosis.

As described above, the ultrasonic diagnostic system shown in FIG. 1 is provided with the computer system 40. On the other hand, the ultrasonic module 200 is provided with the interface and the like which permit data to be transmitted between the computer system 40 and the ultrasonic module 200. This feature makes it possible to readily perform collection of data, editing of data, transmitting and receiving of data, and the like. Further, it is possible to modify also a fine control specification other than predetermined operations through the operation panel 160. Furthermore, the ultrasonic module 200 shown in FIG. 1 is provided with the an ultrasonic diagnostic apparatus 10 shown in FIG. 17 in its entirety. This arrangement permits the ultrasonic module 200 to be separated from the computer system 40. Thus, it is also possible to use the ultrasonic module 200 in a similar fashion to that of the apparatus according to the related art.

Figure 6:
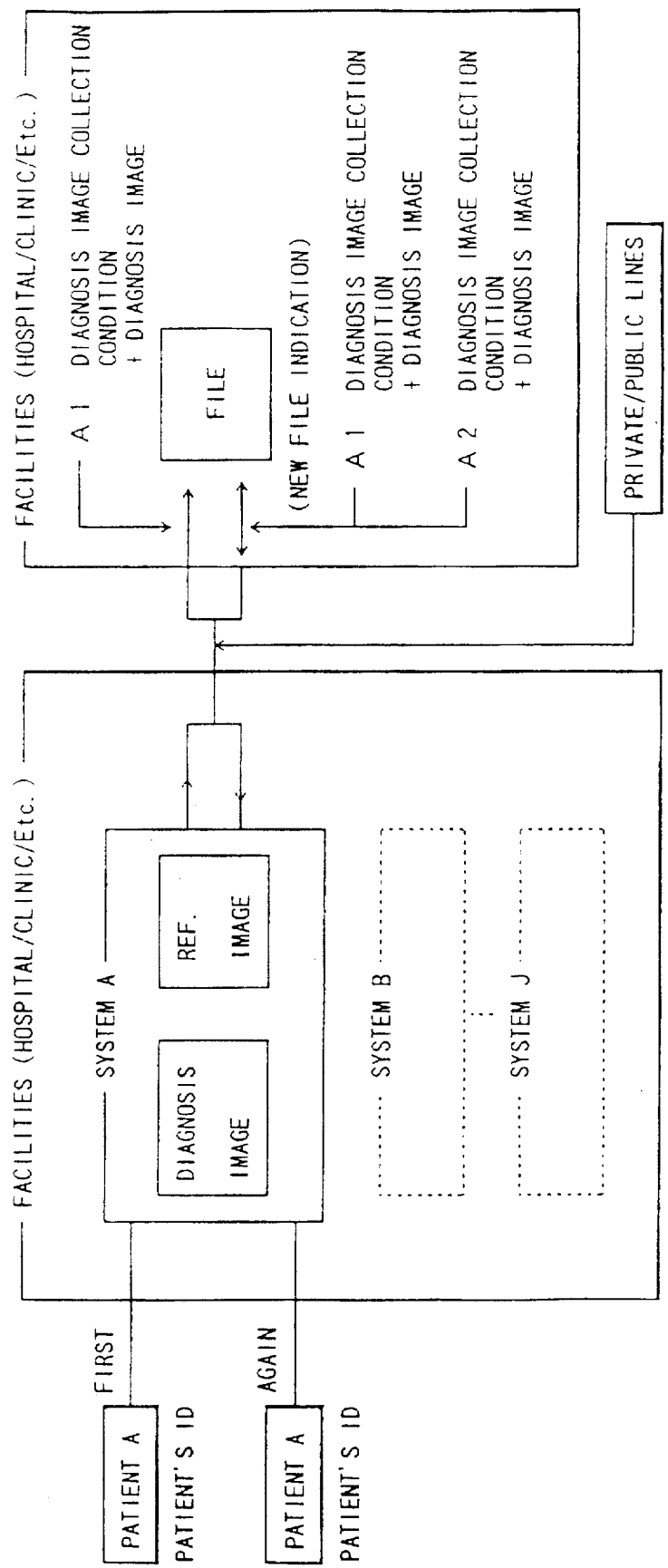
FIG. 6 is a view showing by way of example a broader system in which a plurality of first ultrasonic diagnostic systems shown in FIG. 1 are connected.

FIG. 6 is a view showing by way of example a broader system in which a plurality of first ultrasonic diagnostic systems shown in FIG. 1 are connected.

In this system, there are provided a plurality of systems A to J each analogous to the ultrasonic diagnostic system shown in FIG. 1 in which the filing device is removed or the function of the filing device is reduced, and each being connected through a private line or a public line to a filing system. It is either acceptable that the facilities accommodating the systems A to J is the same as that accommodating the filing system, or is different from that accommodating the filing system.

The images collected in each of the systems A to J are transmitted to the filing system, and are managed in the format of the diagnostic file (part(A) of FIG. 2) in the filing system. The diagnostic file is transferred to the systems A to J in accordance with the necessity.

Also in a case where such a large system is constructed, while it is possible to perform the whole operations explained referring to FIGS. 1 to 5, there will be explained an example (cf. FIG. 3) in which the reference image is displayed placing it beside the diagnostic image.

In case of the first coming in which a patient A first comes to facilities such as a hospital, an operator of an ultrasonic diagnostic system (referred to as a system A) practices the usual operation for the patient A, and transmits the obtained diagnostic images and the image collection conditions involved in the obtained diagnostic images to the filing system. Upon receipt of those messages, the filing system stores and manages those messages in the format of the diagnostic file (part(A) of FIG. 2). When the patient A comes again for the diagnosis, the diagnostic file associated with the previous diagnosis is retrieved on the basis of the patient's ID, so that the image collection conditions in the diagnostic file are transferred to the system system A to be set up in the state suitable for the patient A, and the diagnostic image in the diagnostic file is displayed on the monitor screen in the form of the reference image. This makes it easy to compare the previous diagnostic image with the diagnostic image now collected.

In a case where in spite of the fact that the system A is used to collect the images for the patient A at the previous time, the system A is now used for another patient, another system, for example, a system B may be used for the patient A. In such a case, if the system B is the same as the system A in the specification, the operator can readily regulate the system B to a state near the previous state referring to the reference image.

Figure 7:
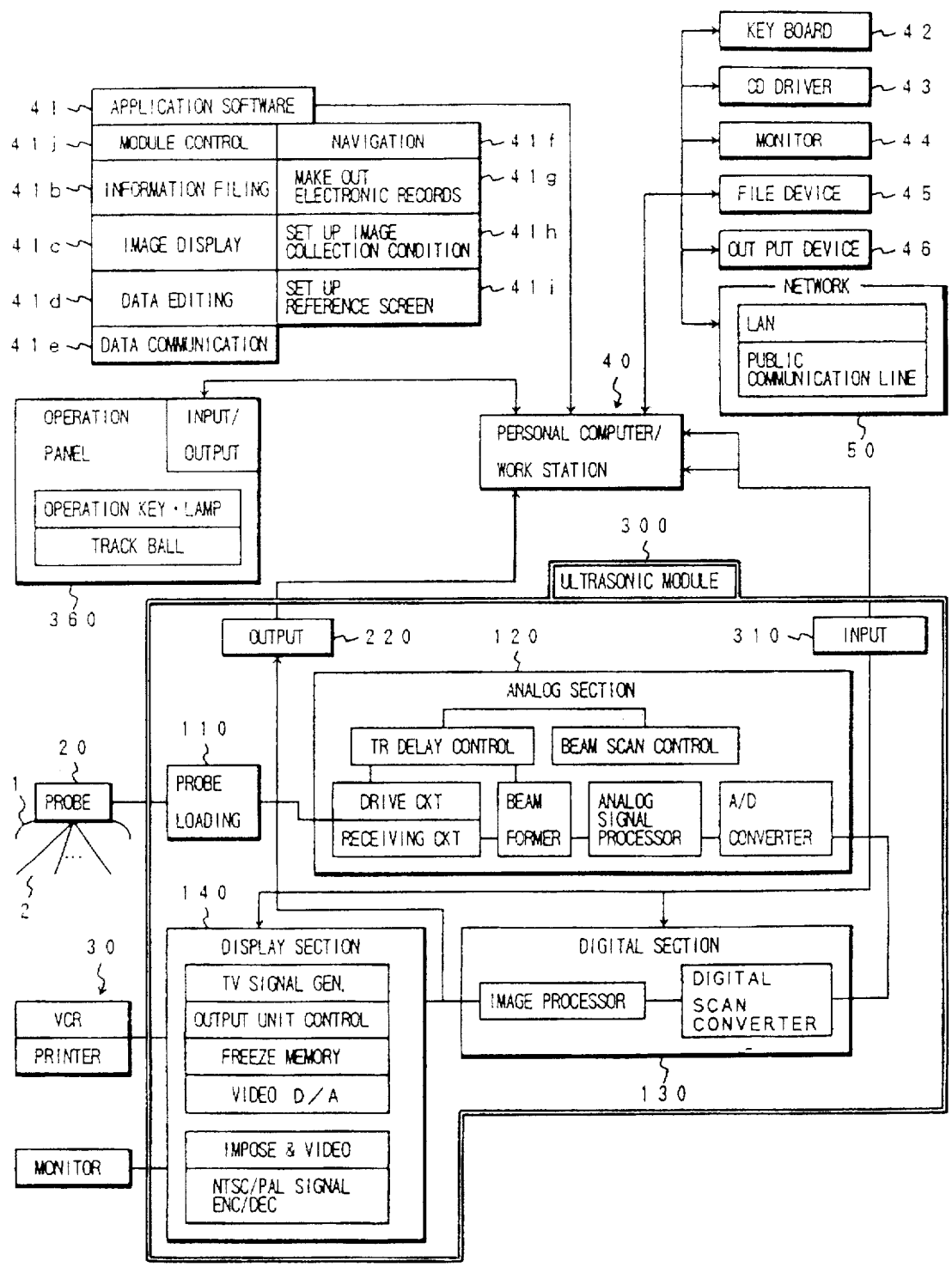
FIG. 7 is a functional block diagram of a second ultrasonic module and a second ultrasonic diagnostic system according to the second embodiment of the present invention.

FIG. 7 is a functional block diagram of a second ultrasonic module and a second ultrasonic diagnostic system according to the second embodiment of the present invention. In FIG. 7, the same parts are denoted by the same reference numbers as those of FIG. 17 and FIG. 1. And the redundant description will be omitted.

In the comparison of the ultrasonic module 300 shown in FIG. 7 with the ultrasonic module 200 shown in FIG. 1, it would be noticed that the ultrasonic module 300 is analogous to one in which the system control unit 150 is removed from the ultrasonic module 200 shown in FIG. 1. Further, in the ultrasonic module 300 shown in FIG. 7, the input unit 210 shown in FIG. 1, which serves to sent the control specification (the operation content of the operation panel 260) from the operation panel 260 through the computer system 40 to the system control unit 150, is replaced by an input unit 310 for receiving a control signal to control the analog section 120, the digital section 130 and the display unit 140 directly with the computer system 40. On the hardware, it is acceptable that the input unit 310 and the output unit 220 similar to that in FIG. 1 are arranged with the same interface or the like. Also in the embodiment shown in FIG. 7, there is provided an operation panel 360 which is the same as the operation panel 260 shown in FIG. 1 in the function. It should be noticed, however, that the operation content of the operation panel 360 is not directly inputted to the ultrasonic module 300, but is send to the computer system 40.

Incidentally, as the operation panel 360, there is assumed one which is especially designed for the ultrasonic diagnostic system. However, it is acceptable to adopt as the operation panel the general information input device, for example, a keyboard and the like, instead of the use of such an especial operation panel 360.

In the application software to be loaded into the computer system 40, there is added a module control routine 41$j$ for directly controlling the ultrasonic module 300 on the basis of the operation content of the operation panel 360, instead of the control specification output routine 41$a$ shown in FIG. 1.

Specifically, in the ultrasonic diagnostic system shown in FIG. 7, the operation content of the operation panel 360 is sent to the computer system 40, and is converted in the computer system 40 into a control signal to control the ultrasonic module 300 in its entirety, that is, the analog section 120, the digital section 130 and the display unit 140. The control signals thus converted are supplied to an input unit 310 of the ultrasonic module 300 and are distributed through the input unit 310 to the respective sections 120, 130 and 140.

According to the ultrasonic diagnostic system shown in FIG. 7, it is impossible to separate only the ultrasonic module 300 and completely operate the same, and thus it is always necessary to operate the ultrasonic module 300 and the computer system 40 in their combination. However, according to the ultrasonic diagnostic system shown in FIG. 7, the ultrasonic module 300 is simple in the structure as compared with the ultrasonic module 200. Further, an alteration of the program for controlling the ultrasonic module makes it possible to readily alter the control of the ultrasonic module. Furthermore, according to the ultrasonic diagnostic system shown in FIG. 7, in a similar fashion to that of the ultrasonic diagnostic system shown in FIG. 1, it is possible to readily perform a collection of data, editing of data, transmitting and receiving of data, and the like.

Figure 8:
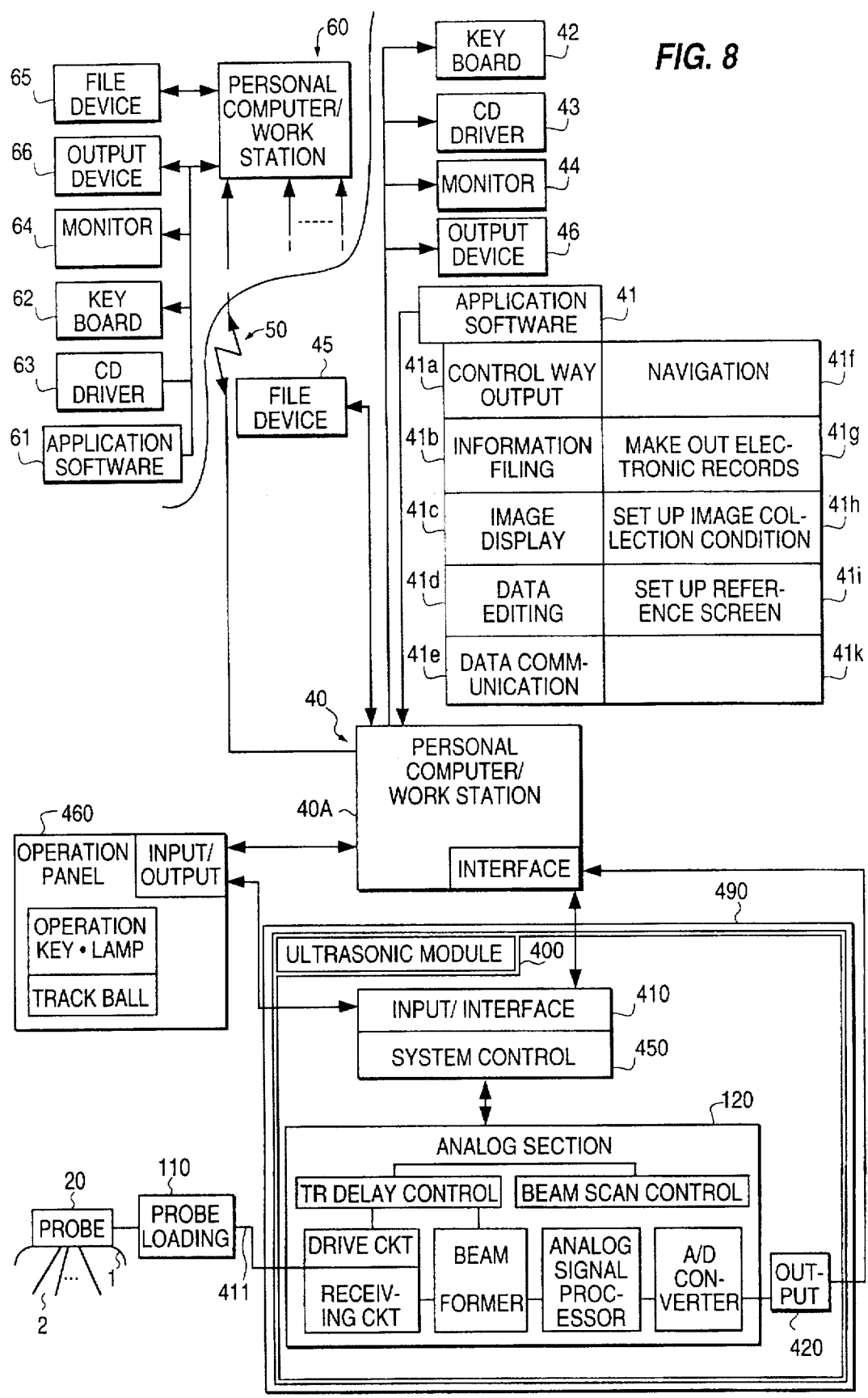
FIG. 8 is a functional block diagram of a third ultrasonic module and a third ultrasonic diagnostic system according to the third embodiment of the present invention.

FIG. 8 is a functional block diagram of a third ultrasonic module and a third ultrasonic diagnostic system according to the third embodiment of the present invention. The difference point from the ultrasonic module and the ultrasonic diagnostic system shown in FIG. 1 will be described hereinafter.

An ultrasonic module 400 shown in FIG. 8 has an analog section 120 similar to that of the ultrasonic module 200, but does not have the digital section 130 and the display unit 140 shown in FIG. 1. Further, connected to the ultrasonic module 400 is no information output device 30. The ultrasonic module 400 shown in FIG. 8 comprises a system control unit 450 and an input section 410 which correspond to the system control unit 150 and the input section 210 in the ultrasonic module 200 shown in FIG. 1, respectively. On the other hand, since the ultrasonic module 400 shown in FIG. 8 is not provided with the digital section 130 and the display unit 140 shown in FIG. 1, the system control unit 450 and the input section 410 serve for the analog section 120 only, specifically, serve to control the analog section 120 only and to receive the control specification for controlling the analog section 120 and transfer the same to the system control unit 450, respectively.

The ultrasonic diagnostic system shown in FIG. 8 has an operation panel 460 provided separately from the ultrasonic module 400, instead of the operation panel 260 incorporated into the ultrasonic module 200 shown in FIG. 1, while their functions are identical to each other. It is acceptable to adopt as the operation panel 460 the general information input device, for example, a keyboard and the like. The operation contents of the operation panel 460 are sent to the computer system 40. Of the operation contents an operation content for a control of the analog section 120 of the ultrasonic module 400 is transferred from the computer system 40 to the input section 410 of the ultrasonic module 400 and then sent to the system control unit 450 so as to be used for a control of the analog section 120. Alternatively, it is acceptable that of the operation contents of the operation panel 460 an operation content for a control of the analog section 120 of the ultrasonic module 400 is directly sent to the ultrasonic module 400 without passing through the computer system 40. Regarding the treatment of the operation content other than the part used in a control of the analog section 120, it will be described later. The signals outputted from the analog section 120 of the ultrasonic module 400 is sent via the output unit 420 to the computer system 40. According to the present embodiment, a probe loading unit 110, which comprises a connector and the like for mounting the ultrasonic probe 20, is provided separately from the ultrasonic module 400. The probe loading unit 110 and the ultrasonic module 400 are connected through a signal line 411.

The ultrasonic module 400 according to the present embodiment is constituted of such small scale of circuit components only, and is formed on a circuit substrate 490.

According to the present embodiment, while the ultrasonic module 400 is mounted on the circuit substrate 490, it is provided separately from the computer system 40. It is acceptable, however, that the circuit substrate 490 is incorporated into the main body 40A of the computer system 40, and the computer system 40 and the ultrasonic module 400 are connected to one another inside of the main body 40A of the computer system 40.

Of the application software 41 to be loaded into the computer system 40 the main ones are: a control specification output routine 41a' for outputting toward the ultrasonic module 400 operation contents used for a control of the analog section 120 of the ultrasonic module 400, of the operation contents entered through the operation panel 460; an information filing routine 41b similar to that in FIG. 1; an image display routine 41c similar to that in FIG. 1; a data editing routine 41d similar to that in FIG. 1; a data communication routine 41e similar to that in FIG. 1; a navigation routine 41f similar to that in FIG. 1; an electronic clinical record making routine 41g similar to that in FIG. 1; an image collection condition setting routine 41h similar to that in FIG. 1; a reference screen setting routine 41i similar to that in FIG. 1; and a digital signal processing routine 41k for practicing the digital signal processing similar to the digital signal processing in the digital section 130 shown in FIG. 1 on the signals outputted from the output unit 420 of the ultrasonic module 400 in accordance with operation contents excepting the portion used for a control of the analog section 120 of the ultrasonic module 400, of the operation contents entered through the operation panel 460.

In this manner, according to the present embodiment, the ultrasonic module 400 is constituted of only the analog section 120 and the peripheral section. This feature makes it possible to contribute to a compactness of the ultrasonic module 400 by mounting the module on a sheet of circuit substrate 490.

The ultrasonic diagnostic system shown in FIG. 8 is provided with an additional computer system 60 connected via the network 50 to the computer system 40. Loaded into the computer system 60 is an application software 61 which is different from the application software 41 of the computer system 40 in the content. The computer system 60 comprises a keyboard 62, a CD driver 63, a monitor device 64, a filing device 65 and an output device 66, which correspond to the keyboard 42, the CD driver 43, the monitor device 44, the filing device 45 and the output device 46 of the computer system 40, respectively. The computer system 60 is connected via the network 50 to a plurality of computer systems each having the similar structure as that of the computer system 40. The computer system 60 manages overall messages transmitted from the plurality of computer systems connected through the network 50.

Figure 9:
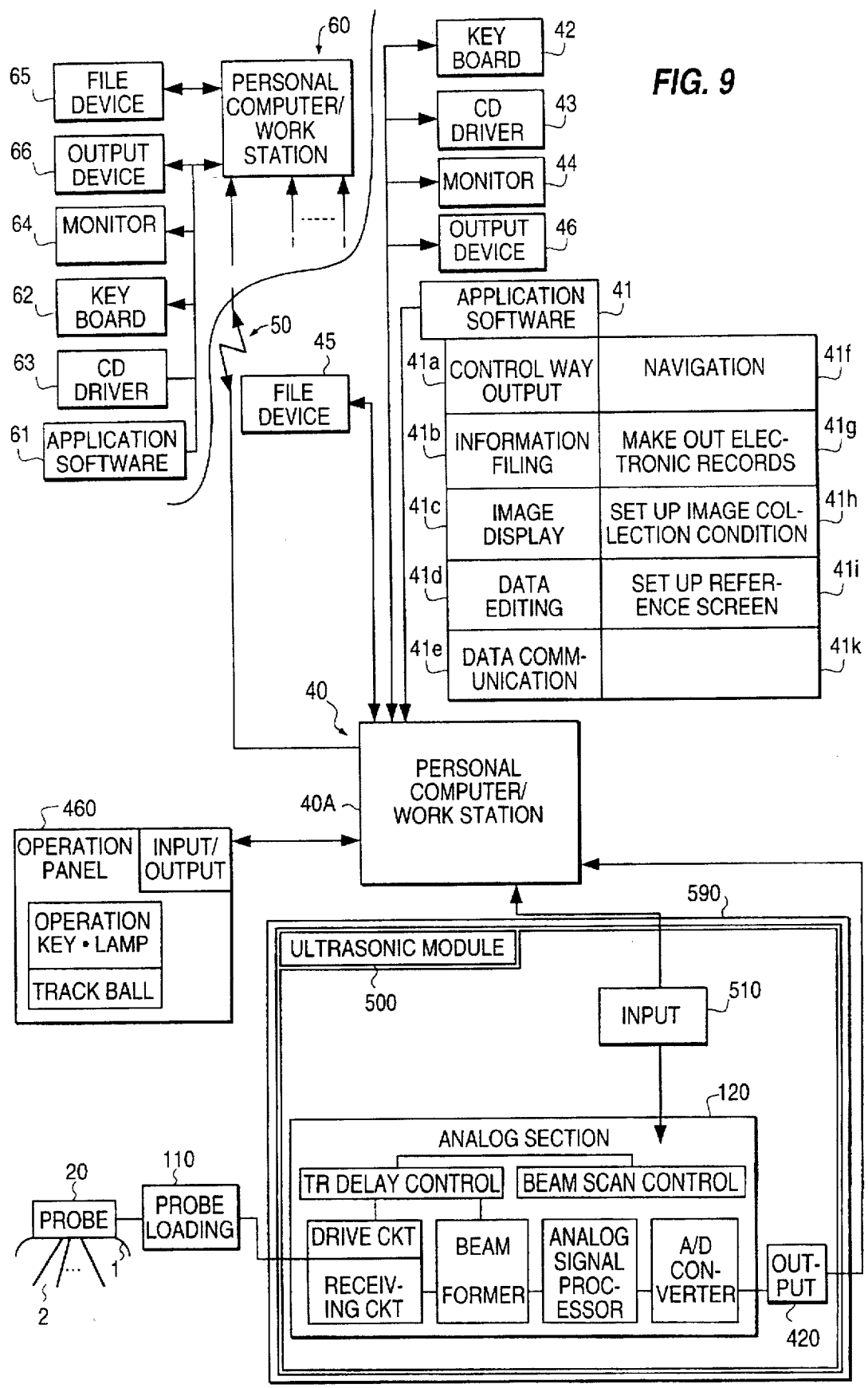
FIG. 9 is a functional block diagram of a fourth ultrasonic module and a fourth ultrasonic diagnostic system according to the fourth embodiment of the present invention.

FIG. 9 is a functional block diagram of a fourth ultrasonic module and a fourth ultrasonic diagnostic system according to the fourth embodiment of the present invention. There will be explained only a difference from the embodiment shown in FIG. 8 hereinafter.

In the comparison of the ultrasonic module 500 shown in FIG. 9 with the ultrasonic module 400 shown in FIG. 8, it would be noticed that the ultrasonic module 500 is analogous to one in which the system control unit 450 is removed from the ultrasonic module 400 shown in FIG. 8. Further, in the ultrasonic module 500 shown in FIG. 9, the input unit 410 shown in FIG. 8, which serves to send the control specification of the analog section 120, is replaced by an input unit 510 for receiving a control signal to control the analog section 120 of the ultrasonic module 500, the control signal being generated by the ultrasonic module control routine 41a' loaded into the computer system 40 on the basis of the operation content of the operation panel 460. Consequently, in the ultrasonic module 500 shown in FIG. 9, the circuit scale can be reduced as compared with the ultrasonic module 400 shown in FIG. 8, and thus the ultrasonic module 500 shown in FIG. 9 is mounted on the smaller circuit substrate 590.

Other arrangement of the ultrasonic diagnostic system shown in FIG. 9 is similar to that of the ultrasonic diagnostic system shown in FIG. 8.

Figure 10:
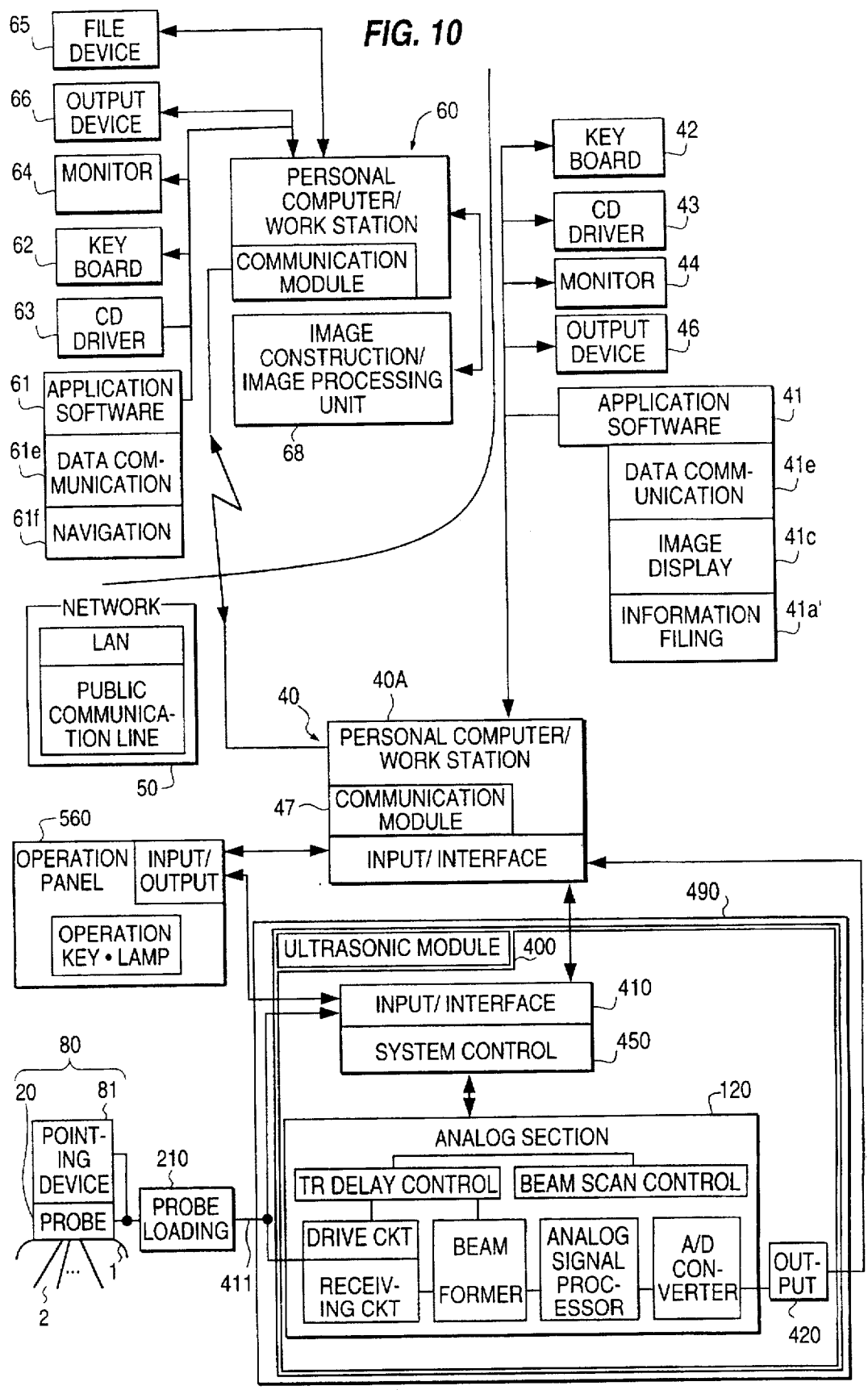
FIG. 10 is a functional block diagram of a fifth ultrasonic diagnostic system according to the fifth embodiment of the present invention.

FIG. 10 is a functional block diagram of a fifth ultrasonic diagnostic system according to the fifth embodiment of the present invention. There will be explained only a difference from the embodiment shown in FIG. 8 hereinafter.

The ultrasonic diagnostic system shown in FIG. 10 is provided with the first computer system 40 and the second computer system 60 which are connected to each other through the communication line 50. The first computer system 40 transmits ultrasonic data collected by the ultrasonic module 400 to the computer system 60 in their present form by a communication module 47 and the data communication routine 41e in the application software 41. The computer system 60 is provided with an image construction/image processing unit 68. The computer system 60 receives ultrasonic data transmitted thereto by a communication module 67 and the data communication routine 61e, and transmits the received ultrasonic data to the image construction/image processing unit 68. The image construction/image processing unit 68 practices the processing equivalent to the digital processing described referring to FIG. 1 on the received ultrasonic data to construct images. Alternatively, the image construction/image processing unit 68 practices the image processing on the images thus constructed to construct images further excellent in a diagnostic applicability. The images thus constructed are stored in the form of the diagnostic file (part (A) of FIG. 2) in the filing device 65 of the computer system 60 end. Hence, at the computer system 40 there is provided no filing device for storing the diagnostic file.

In an operation panel 560 shown in FIG. 10, there is omitted a track ball which is provided in the operation panel 460 shown in FIG. 8. Instead, there is provided a pointing device 81 for a position designation on the screen in one united body with the probe 20. The pointing device 81 has a similar structure to that of the track ball. They constitute an ultrasonic probe 80 in the form of a unitary body.

Figure 11:
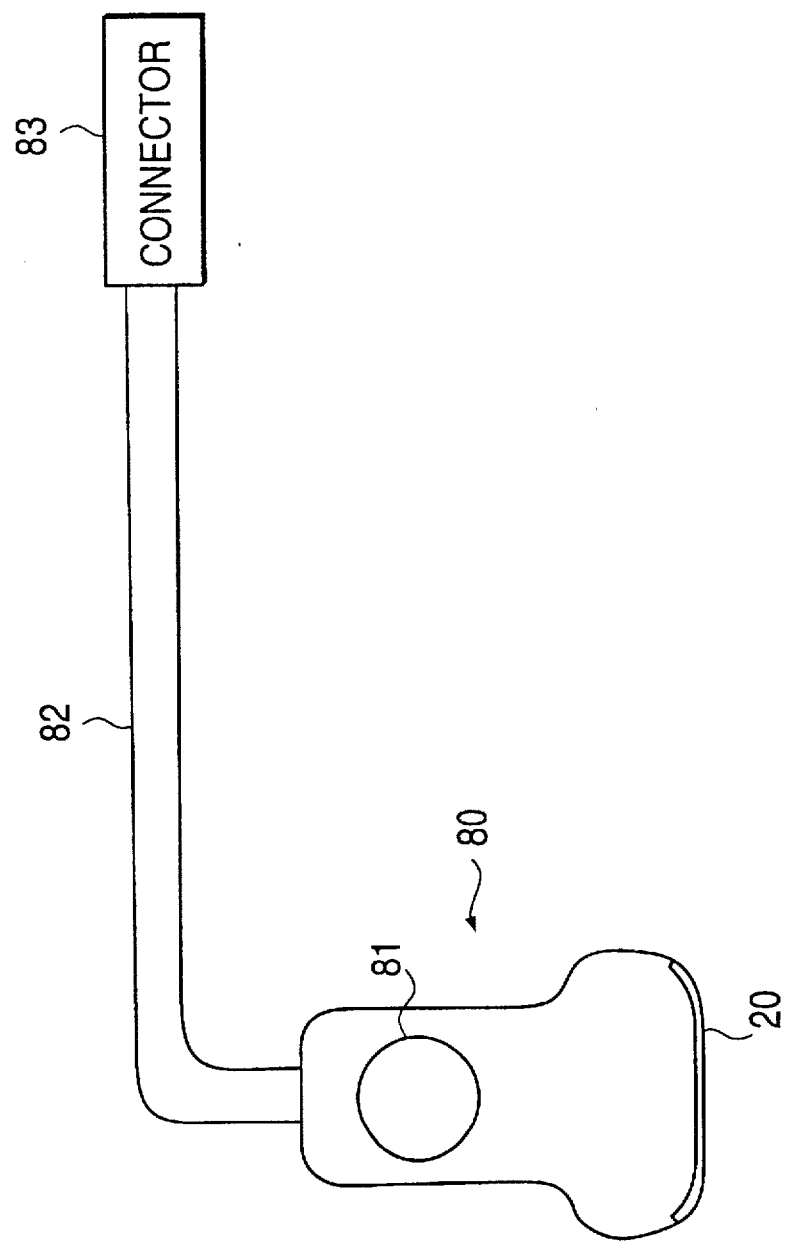
FIG. 11 is a perspective view of an ultrasonic probe.

FIG. 11 is a perspective view of an ultrasonic probe 80 shown in FIG. 10.

The tip of the head of the ultrasonic probe 80 is provided with a probe 20. The head is provided with the pointing device 81 having a structure similar to the track ball. These probe 20 and pointing device 81 and the probe loading unit 210 are connected through the cable 82 and the connector 83. The probe loading unit 210 distributes, as shown in FIG. 10, the signal line connected to the probe 20 and the signal line connected to the pointing device 81 to the analog section 120 and the interface 410, respectively. The interface 410 sends out the signal received from the pointing device 81 to the computer system 40.

Thus, providing pointing device 81 on the ultrasonic probe 80 makes it possible to operate the pointing device while performing an operation for collecting the ultrasonic data putting the probe 20 on the surface of the body of the patient 20, thereby contributing to the improvement of the operability.

According to the ultrasonic diagnostic system shown in FIG. 10, at the computer system 60 end, the navigation routine 61f is actuated, so that the above-mentioned operation guide, navigation image and the like are transmitted via the network 50 to the computer system 40, prior to collection of the ultrasonic data at the computer system 40 end. On the other hand, at the computer system 40 end, the image display routine 41c is actuated, so that the navigation images and the like are displayed on the display screen of the monitor device 44 of the computer system 40 end.

Also the images build at the computer system 60 end are transmitted via the network 50 to the computer system 40 end, and are displayed on the display screen of the monitor device 44 of the computer system 40 end.

Further, the electronic clinic records are also made out at the computer system 60 end, and transmitted to the computer system 40 end if necessary.

As apparent from the above-mentioned matter, according to the present embodiment, a part is shared into a collection of ultrasonic data at the computer system 40 end and a diagnosis at the computer system 60 end. Thus, this feature allows, for example, such a situation that the computer system 40 is loaded on a group examination car or is carried in homes to collect ultrasonic data, and a diagnosis according to the collected ultrasonic data is performed, for example, at the hospital in which the computer system 60 is installed.

Figure 12:
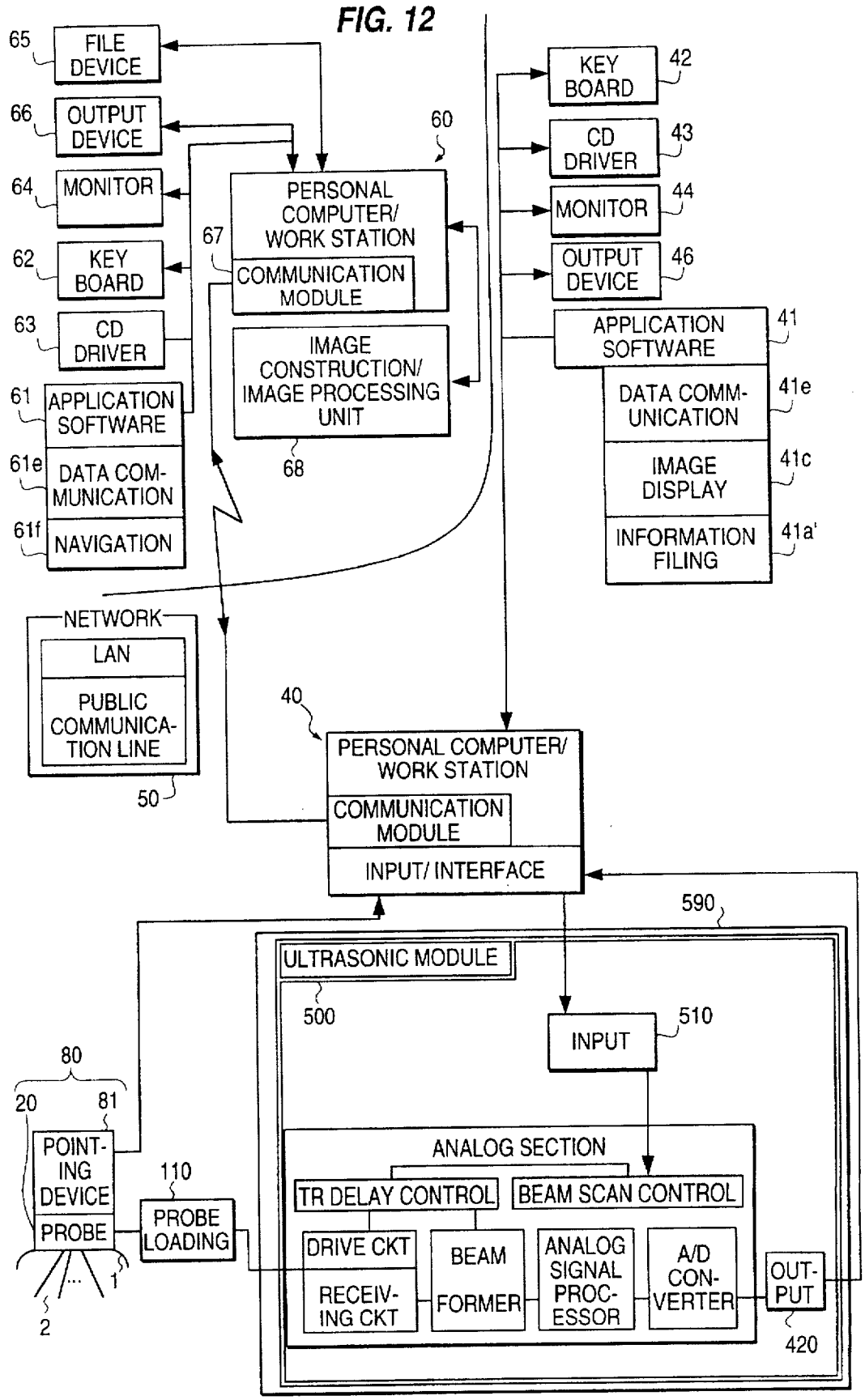
FIG. 12 is a functional block diagram of a sixth ultrasonic diagnostic system according to the sixth embodiment of the present invention.

FIG. 12 is a functional block diagram of a sixth ultrasonic diagnostic system according to the sixth embodiment of the present invention. There will be explained only a difference from the ultrasonic diagnostic systems shown in FIGS. 9 and 10, hereinafter.

An ultrasonic module 500 is the same as that shown in FIG. 9. The computer system 40 causes the module control routine 41a' to be actuated so as to send out to the ultrasonic module 500 a control signal to control the analog section 120 of the ultrasonic module 500. But, different from the ultrasonic diagnostic systems shown in FIG. 9, the computer system 40 is provided with no especial operation panel. The keyboard 42 is used also as the operation panel.

Figure 13:
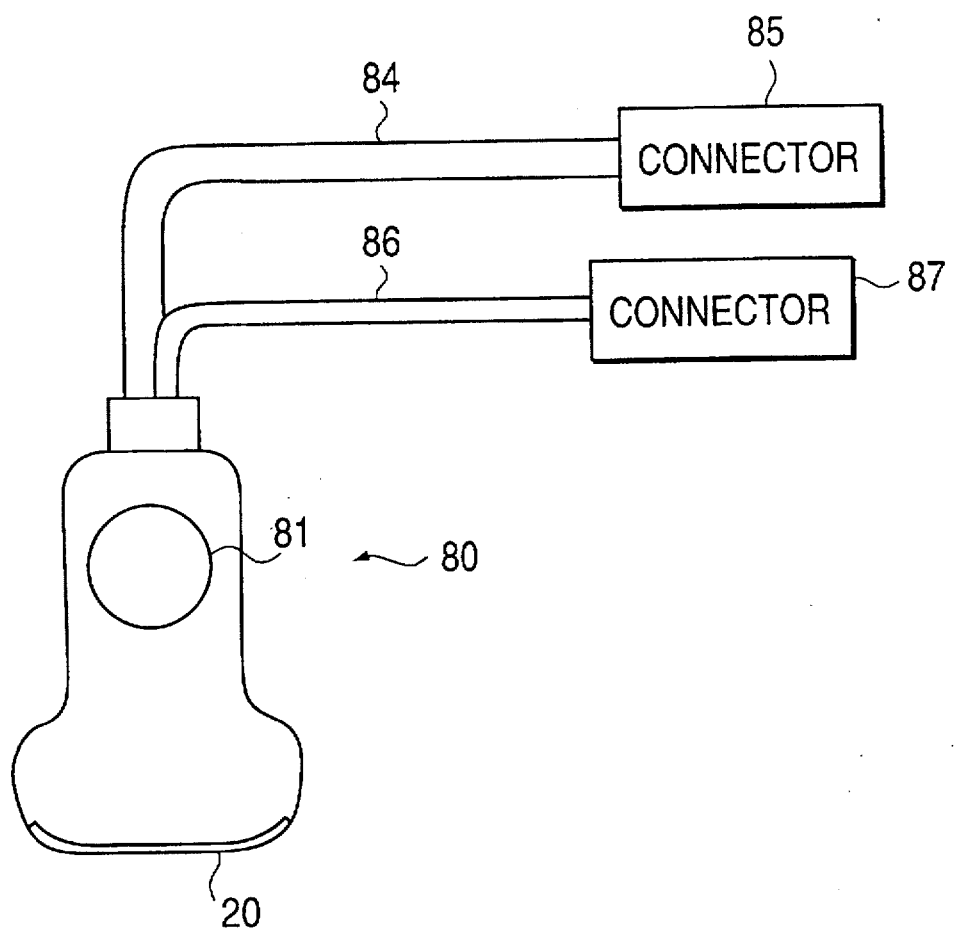
FIG. 13 is a perspective view of an ultrasonic probe.

FIG. 13 is a perspective view of an ultrasonic probe 80 shown in FIG. 12.

In the ultrasonic probe 80, the structure of the head having the probe 20 and the pointing device 81 is the same as the ultrasonic probe shown in FIG. 11. But the cable and connector are divided into cable 84 and connector 85 connected to the probe 20; and cable 86 and connector 87 connected to the pointing device 81. The connector 85 is mounted on the probe loading unit 110, while the connector 87 is mounted directly on the computer system 40.

Figure 14:
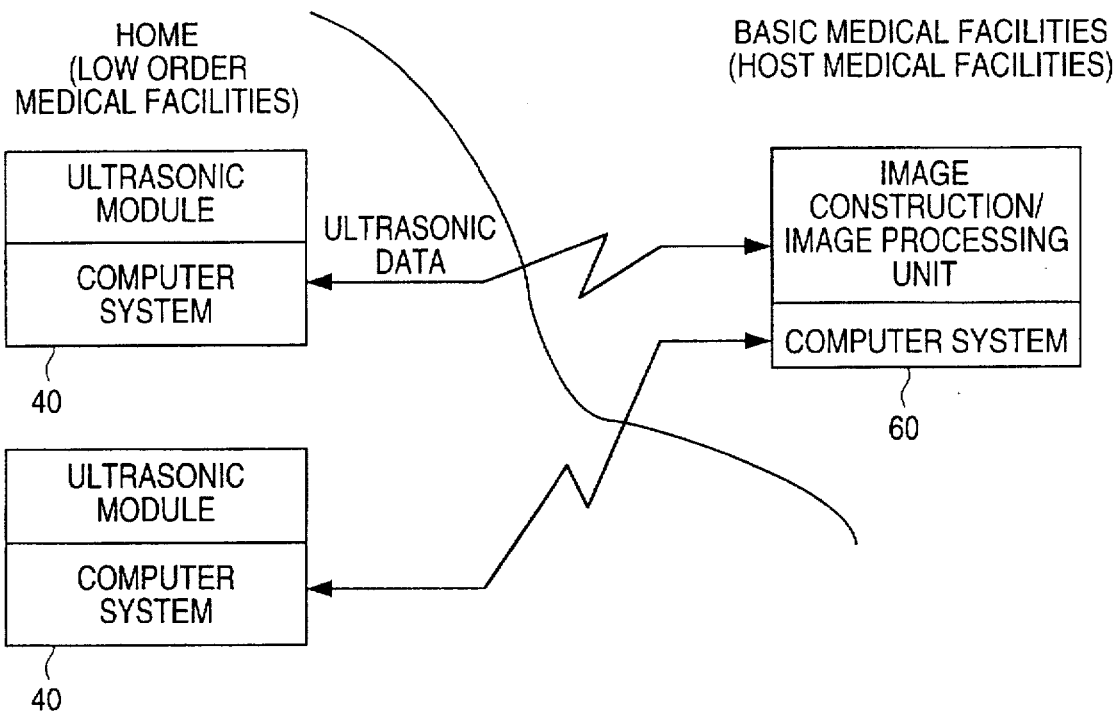
FIG. 14 is an illustration showing by way of example an application of the ultrasonic diagnostic system shown in FIG. 10 or 12.

FIG. 14 is an illustration showing by way of example an application of the ultrasonic diagnostic system shown in FIG. 10 or 12.

The computer system 60 is installed at the basic medical facilities, for example, a hospital or the like, while the computer system 40 and the associated ultrasonic module may be carried in homes or group examination cars. In FIG. 14, there is shown a state that a plurality of computer systems 40 are connected through the communication line to the computer system 60.

It is desired for a portable computer system 40 (including an ultrasonic module) that the system is of compactness and lightweight, capable of collecting a high quality of ultrasonic data, and of low cost. Only an implementing means for satisfying this requirement is, as shown in FIG. 14, the ultrasonic diagnostic system of a separation type in which a terminal device end (e.g. computer system 40) is loaded with only functions necessary for deriving ultrasonic data from a patient, and other image processing function, image construction function and the like are left to the basic system (e.g. computer system 60). According to the aspect of this scheme, a high quality of images is constructed at the basic computer system 60, and it is possible to incorporate thereinto all functions effective for the diagnosis.

According to ultrasonic diagnostic system of the present invention, it is possible to provide an opportunity of having an ultrasonic diagnosis also for patients in areas wherein the medical facilities are poor.

Figure 15:
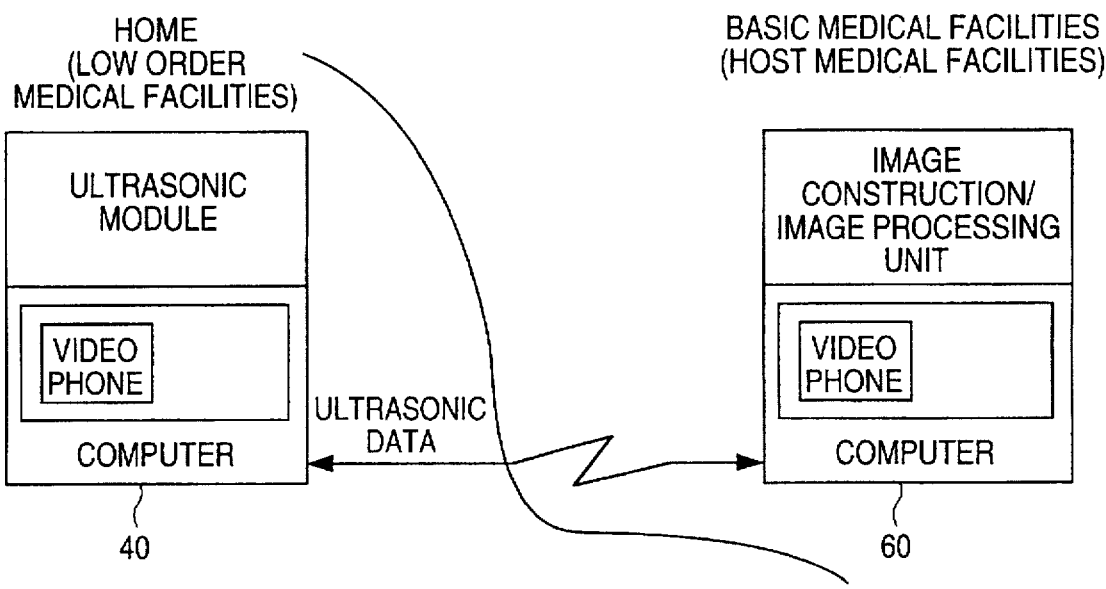
FIGS. 15 and 16 are each an illustration showing a modification of that shown in FIG. 14 in which only one computer system 40 is shown and others are omitted.
Figure 16:
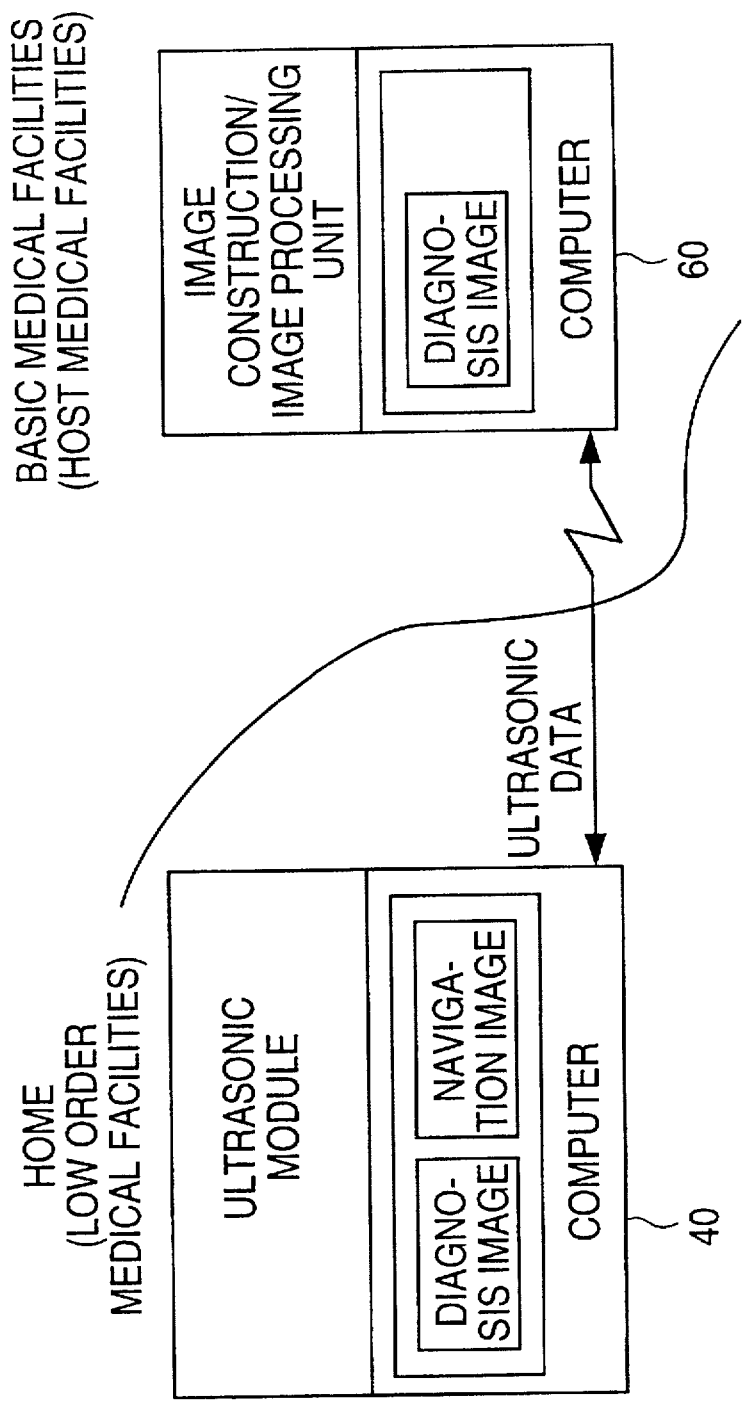

FIGS. 15 and 16 are each an illustration showing a modification of that shown in FIG. 14 in which only one computer system 40 is shown and others are omitted.

When the probe is handled to derive ultrasonic data, it becomes a problem whether a section of scanning of ultrasonic beams is of the intended site. For this reason, the computer system 40 is connected through a video phone to the computer system 60, so that an operator at the computer system 40 end may obtain ultrasonic data through contacting with a doctor or an examination engineer at the computer system 60 end.

In this manner, at the computer system 40 end, it is possible to obtain ultrasonic data involved in the section of the intended site and transmit such ultrasonic data to the computer system 60.

FIG. 16 illustrates an example in which a navigation image is displayed together with a diagnostic image at the computer system 40 end.

Regarding the navigation images, it is acceptable that as mentioned above, the navigation image, which is stored beforehand in the CD, is loaded at the computer system 40 end. Alternatively, it is acceptable that prior to deriving the ultrasonic data, the navigation images are transmitted from the computer system 60 to the computer system 40.

According to constructing the ultrasonic diagnostic systems as shown in FIGS. 14-16, the doctor in charge of the diagnosis may make a decision through confirming images constructed at the computer system 60 end on the basis of the ultrasonic data transmitted via the communication line, even if he is not at the medical scene (computer system 40 end), and describe his messages in electronic clinical records, and return the electronic clinical record to the medical scene. The system mentioned above is effective also in a case where a further diagnosis on the obtained ultrasonic diagnostic information is requested to a host hospital or a medical specialist.

As mentioned above, according to the present invention, there is constructed an ultrasonic diagnostic system capable of performing a communication of ultrasonic data, wherein for example, the general-purpose use of personal computer and workstation are connected thereto to readily perform data collection, editing, data communication and the like.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An ultrasonic module adapted for use in an ultrasonic diagnostic system including an operation panel and a computer system that outputs a control signal for controlling said ultrasonic module, the control signal being generated based on a control specification entered through said operation panel, said ultrasonic module comprising:

an analog unit for supplying drive signals for a transmission of ultrasonic waves to an ultrasonic probe adapted for transmitting and receiving ultrasonic waves, and for practicing an analog signal processing on received signals obtained through said ultrasonic probe;

a digital unit for practicing a digital signal processing on signals generated from said analog unit;

a display circuit unit for practicing a processing for causing an image display to display an image based on signals generated from said digital unit;

a system control unit for controlling said analog unit, said digital unit, and said display circuit unit;

an input unit for inputting a control specification issued from an exterior to said system control unit; and an output unit for outputting the signals generated from said digital unit to an exterior, wherein all of said units are incorporated in one united body.

2. An ultrasonic module adapted for use in an ultrasonic diagnostic system including a computer system that outputs a control signal to the ultrasonic module, said ultrasonic module comprising:

an analog unit for supplying signals for a transmission of ultrasonic waves to an ultrasonic probe adapted for transmitting and receiving ultrasonic waves, and for practicing an analog signal processing on received signals obtained through said ultrasonic probe;

an input unit for inputting a control signal to control said analog unit; and an output unit for outputting signals generated from said analog unit to an exterior, wherein all of said units are incorporated in one united body.

3. An ultrasonic diagnostic system comprising:

an ultrasonic module comprising: an analog unit for supplying drive signals for a transmission of ultrasonic waves to an ultrasonic probe adapted for transmitting and receiving ultrasonic waves, and for practicing an analog signal processing on received signals obtained through said ultrasonic probe; a digital unit for practicing a digital signal processing on signals generated from said analog unit; a display circuit unit for practicing a processing for causing an image display to display an image based on signals generated from said digital unit; a system control unit for controlling said analog unit, said digital unit and said display circuit unit; an input unit for inputting a control specification issued from an exterior to said system control unit; and an output unit for outputting the signals generated from said digital unit to an exterior, wherein all of said units are incorporated in one united body;

an operation panel in which incorporated thereinto are an operation panel unit for inputting an instruction as to a control specification for a control of said analog unit, said digital unit and said display circuit unit in said system control unit, and an additional output unit for outputting the control specification produced through an operation by said operation panel unit to an exterior; and a computer system connected to said input unit and said output unit of said ultrasonic module, and also to said additional output unit of said operation panel, said computer system being capable of performing an output of a control signal for controlling said ultrasonic module generated based on the control specification entered through said operation panel, a filing of information based on signals generated from said output unit, and a display of images based on the signals generated from said output unit.

4. An ultrasonic diagnostic system according to claim 3, wherein said computer system comprises:

diagnostic file producing means for producing a diagnostic file, on each diagnosis for each patient, containing at least patient ID information for discriminating patients, one or more sheets of image produced on the basis of signals generated from said ultrasonic module, and image collection conditions representative of a state of said ultrasonic module involved in a time when the signals, on the basis of which the images are produced, are obtained in said ultrasonic module; and editing means for extracting and collecting information based on a designated editing specification from among a plurality of diagnostic files produced by said diagnostic file producing means.

5. An ultrasonic diagnostic system according to claim 4, wherein said computer system comprises:

electronic clinical record producing means for producing an electronic clinical record containing one's view as to said diagnostic file, an image extracted from said diagnostic file, and a line drawing image produced on the basis of the image extracted from said diagnostic file.

6. An ultrasonic diagnostic system according to claim 4, wherein said computer system comprises:

diagnostic condition setting means for transmitting, at a time of a re-examination to again obtain signals for producing images, using said ultrasonic module, on a patient specified by the patient ID recorded in anyone of the diagnostic files produced at the past, image collection conditions recorded on the diagnostic file produced at the past on the same patient to said ultrasonic module.

7. An ultrasonic diagnostic system according to claim 4, wherein said computer system comprises:

image display means for displaying, at a time of a re-examination to again obtain signals for producing images, using said ultrasonic module, on a patient specified by the patient ID recorded in anyone of the diagnostic files produced at the past, image recorded on the diagnostic file produced at the past on the same patient.

8. An ultrasonic diagnostic system according to claim 3, wherein said computer system comprises:

navigation image display means for displaying a navigation image to support an operation for deriving images using said ultrasonic module.

9. An ultrasonic diagnostic system according to claim 3, wherein said ultrasonic diagnostic system includes said ultrasonic probe, a pointing device for designating a position on a screen, and a cable for carrying a transmission of signals transferred between said ultrasonic probe and said pointing device and said ultrasonic module.

10. An ultrasonic diagnostic system according to claim 3, wherein said ultrasonic diagnostic system includes said ultrasonic probe, a pointing device for designating a position on a screen, and a first cable for carrying a transmission of signals transferred between said ultrasonic probe and said ultrasonic module, and a second cable for carrying a transmission of signals transferred between said pointing device and said computer system.

11. An ultrasonic diagnostic system comprising:

an ultrasonic module comprising: an analog unit for supplying signals for a transmission of ultrasonic waves to an ultrasonic probe adapted for transmitting and receiving ultrasonic waves, and for practicing an analog signal processing on received signals obtained through said ultrasonic probe; an input unit for inputting a control signal to control said analog unit; and an output unit for outputting signals generated from said analog unit to an exterior, wherein all of said units are incorporated in one united body; and a computer system connected to said input unit and said output unit of said ultrasonic module, said computer system being capable of performing an output of a control signal for controlling said ultrasonic module, a digital signal processing to be practiced on signals generated from said ultrasonic module, a filing of information based on signals subjected to the digital signal processing, and a display of images based on the signals subjected to the digital signal processing.

12. An ultrasonic diagnostic system according to claim 11, wherein said computer system comprises:

diagnostic file producing means for producing a diagnostic file, on each diagnosis for each patient, containing at least patient ID information for discriminating patients, one or more sheets of image produced on the basis of signals generated from said ultrasonic module, and image collection conditions representative of a state of said ultrasonic module involved in a time when the signals, on the basis of which the images are produced, are obtained in said ultrasonic module; and editing means for extracting and collecting information based on a designated editing specification from among a plurality of diagnostic files produced by said diagnostic file producing means.

13. An ultrasonic diagnostic system according to claim 12, wherein said computer system comprises:

electronic clinical record producing means for producing an electronic clinical record containing one's view as to said diagnostic file, an image extracted from said diagnostic file, and a line drawing image produced on the basis of the image extracted from said diagnostic file.

14. An ultrasonic diagnostic system according to claim 12, wherein said computer system comprises:

diagnostic condition setting means for transmitting, at a time of a re-examination to again obtain signals for producing images, using said ultrasonic module, on a patient specified by the patient ID recorded in anyone of the diagnostic files produced at the past, image collection conditions recorded on the diagnostic file produced at the past on the same patient to said ultrasonic module.

15. An ultrasonic diagnostic system according to claim 12, wherein said computer system comprises:

image display means for displaying, at a time of a re-examination to again obtain signals for producing images, using said ultrasonic module, on a patient specified by the patient ID recorded in anyone of the diagnostic files produced at the past, image recorded on the diagnostic file produced at the past on the same patient.

16. An ultrasonic diagnostic system according to claim 11, wherein said computer system comprises:

navigation image display means for displaying a navigation image to support an operation for deriving images using said ultrasonic module.

17. An ultrasonic diagnostic system according to claim 11, wherein said ultrasonic diagnostic system includes said ultrasonic probe, a pointing device for designating a position on a screen, and a cable for carrying a transmission of signals transferred between said ultrasonic probe and said pointing device and said ultrasonic module.

18. An ultrasonic diagnostic system according to claim 11, wherein said ultrasonic diagnostic system includes said ultrasonic probe, a pointing device for designating a position on a screen, and a first cable for carrying a transmission of signals transferred between said ultrasonic probe and said ultrasonic module, and a second cable for carrying a transmission of signals transferred between said pointing device and said computer system.

19. An ultrasonic diagnostic system comprising:

an ultrasonic module including:

an analog unit for supplying drive signals for a transmission of ultrasonic waves to an ultrasonic probe adapted for transmitting and receiving ultrasonic waves, and for practicing an analog signal processing on received signals obtained through said ultrasonic probe;

a digital unit for practicing a digital signal processing on signals generated from said analog unit;

a display circuit unit for practicing a processing for causing an image display to display an image based on signals generated from said digital unit;

a system control unit for controlling said analog unit, said digital unit, and said display circuit unit;

an operation panel unit for inputting an instruction as to a control specification to said system control unit;

an input unit for inputting a control specification issued from an exterior to said system control unit; and an output unit for outputting the signals generated from said digital unit to an exterior, wherein all of said units are incorporated in one united body; and a computer system connected to said input unit and said output unit of said ultrasonic module, said computer system being capable of performing an output of a control specification for controlling said ultrasonic module, a filing of information based on signals generated from said output unit, and a display of images based on the signals generated from said output unit, wherein said computer system includes:

diagnostic file producing means for producing a diagnostic file, on each diagnosis for each patient, containing at least one patient ID information for discriminating patients, one or more sheets of image produced on the basis of signals generated from said ultrasonic module, and image collection conditions representative of a state of said ultrasonic module involved in a time when the signals, on the basis of which the images are produced, are obtained in said ultrasonic module; and editing means for extracting and collecting information based on a designated editing specification from among a plurality of diagnostic files produced by said diagnostic file producing means.

20. An ultrasonic diagnostic system according to claim 19, wherein said computer system comprises:

electronic clinical record producing means for producing an electronic clinical record containing one's view as to said diagnostic file, an image extracted from said diagnostic file, and a line drawing image produced on the basis of the image extracted from said diagnostic file.

21. An ultrasonic diagnostic system according to claim 19, wherein said computer system comprises:

diagnostic condition setting means for transmitting, at a time of a re-examination to again obtain signals for producing images, using said ultrasonic module, on a patient specified by the patient ID recorded in anyone of the diagnostic files produced at the past, image collection conditions recorded on the diagnostic file produced at the past on the same patient to said ultrasonic module.

22. An ultrasonic diagnostic system according to claim 19, wherein said computer system comprises:

image display means for displaying, at a time of a re-examination to again obtain signals for producing images, using said ultrasonic module, on a patient specified by the patient ID recorded in anyone of the diagnostic files produced at the past, image recorded on the diagnostic file produced at the past on the same patient.

23. An ultrasonic diagnostic system comprising:
an ultrasonic module including:
an analog unit for supplying signals for a transmission of ultrasonic waves to an ultrasonic probe adapted for transmitting and receiving ultrasonic waves, and for practicing an analog signal processing on received signals obtained through said ultrasonic probe;

a system control unit for controlling said analog unit; and an output unit for outputting signals generated from said analog unit to an exterior, wherein all of said units are incorporated in one united body; and a computer system connected to said output unit of said ultrasonic module, said computer system being capable of performing a digital signal processing to be practiced on signals generated from said ultrasonic module, a filing of information based on signals subjected to the digital signal processing, and a display of images based on the signals subjected to the digital signal processing, wherein said computer system includes:

diagnostic file producing means for producing a diagnostic file, on each diagnosis for each patient, containing at least one patient ID information for discriminating patients, one or more sheets of image produced on the basis of signals generated from said ultrasonic module, and image collection conditions representative of a state of said ultrasonic module involved in a time when the signals, on the basis of which the images are produced, are obtained in said ultrasonic module; and editing means for extracting and collecting information based on a designated editing specification from among a plurality of diagnostic files produced by said diagnostic file producing means.

24. An ultrasonic diagnostic system according to claim 23, wherein said computer system comprises:

electronic clinical record producing means for producing an electronic clinical record containing one's view as to said diagnostic file, an image extracted from said diagnostic file, and a line drawing image produced on the basis of the image extracted from said diagnostic file.

25. An ultrasonic diagnostic system according to claim 23, wherein said computer system comprises:

diagnostic condition setting means for transmitting, at a time of a re-examination to again obtain signals for producing images, using said ultrasonic module, on a patient specified by the patient ID recorded in anyone of the diagnostic files produced at the past, image collection conditions recorded on the diagnostic file produced at the past on the same patient to said ultrasonic module.

26. An ultrasonic diagnostic system according to claim 23, wherein said computer system comprises:

image display means for displaying, at a time of a re-examination to again obtain signals for producing images, using said ultrasonic module, on a patient specified by the patient ID recorded in anyone of the diagnostic files produced at the past, image recorded on the diagnostic file produced at the past on the same patient.

27. An ultrasonic diagnostic system comprising:
an ultrasonic module including:
an analog unit for supplying drive signals for a transmission of ultrasonic waves to an ultrasonic probe adapted for transmitting and receiving ultrasonic waves, and for practicing an analog signal processing on received signals obtained through said ultrasonic probe;

a digital unit for practicing a digital signal processing on signals generated from said analog unit;

a display circuit unit for practicing a processing for causing an image display to display an image based on signals generated from said digital unit;

a system control unit for controlling said analog unit, said digital unit, and said display circuit unit;

an operation panel unit for inputting an instruction as to a control specification to said system control unit;

an input unit for inputting a control specification issued from an exterior to said system control unit; and an output unit for outputting the signals generated from said digital unit to an exterior, wherein all of said units are incorporated in one united body; and a computer system connected to said input unit and said output unit of said ultrasonic module, said computer system being capable of performing an output of a control specification for controlling said ultrasonic module, a filing of information based on signals generated from said output unit, and a display of images based on the signals generated from said output unit, wherein said computer system includes:

navigation image display means for displaying a navigation image to support an operation for deriving images using said ultrasonic module.

28. An ultrasonic diagnostic system comprising:

an ultrasonic module including:

an analog unit for supplying signals for a transmission of ultrasonic waves to an ultrasonic probe adapted for transmitting and receiving ultrasonic waves, and for practicing an analog signal processing on received signals obtained through said ultrasonic probe;

a system control unit for controlling said analog unit; and an output unit for outputting signals generated from said analog unit to an exterior, wherein all of said units are incorporated in one united body; and a computer system connected to said output unit of said ultrasonic module, said computer system being capable of performing a digital signal processing to be practiced on signals generated from said ultrasonic module, a filing of information based on signals subjected to the digital signal processing, and a display of images based on the signals subjected to the digital signal processing, wherein said computer system includes:

navigation image display means for displaying a navigation image to support an operation for deriving images using said ultrasonic module.

29. An ultrasonic diagnostic system comprising:

an ultrasonic module including:

an analog unit for supplying signals for a transmission of ultrasonic waves to an ultrasonic probe adapted for transmitting and receiving ultrasonic waves, and for practicing an analog signal processing on received signals obtained through said ultrasonic probe;

a system control unit for controlling said analog unit;

an output unit for outputting the signals generated from said analog unit to an exterior, wherein all of said units are incorporated in one united body;

a first computer system connected to said output unit of said ultrasonic module, said computer system being capable of performing a data communication, via a communication line, including a transmission of signals output from said ultrasonic module; and a second computer system connected via said communication line to said first computer system, said second computer system being capable of performing a data communication including a reception of the signals output from said ultrasonic module and transmitted from said first computer system, and also being capable of producing images based on received signals, wherein said second computer system includes:

transmitting means for transmitting to said first computer system a signal representative of a navigation image to support an operation for deriving images using said ultrasonic module, and wherein said first computer system includes:

receiving means for receiving the signal representative of the navigation image transmitted from said second computer system; and navigation image display means for displaying the navigation image based on received signals.

30. An ultrasonic diagnostic system according to claim 29, wherein said ultrasonic diagnostic system comprises an ultrasonic probe device having an ultrasonic probe for transmitting and receiving ultrasonic waves, a pointing device for designating a position on a screen, and a cable for carrying a transmission of signals transferred between said ultrasonic probe and said pointing device and said ultrasonic module.

31. An ultrasonic diagnostic system according to claim 29, wherein said ultrasonic diagnostic system comprises an ultrasonic probe device having an ultrasonic probe for transmitting and receiving ultrasonic waves, a pointing device for designating a position on a screen, a first cable for carrying a transmission of signals transferred between said ultrasonic probe and said ultrasonic module, and a second cable for carrying a transmission of signals transferred between said pointing device and said first computer system.

32. An ultrasonic diagnostic system comprising:

an ultrasonic module including:

an analog unit for supplying signals for a transmission of ultrasonic waves to an ultrasonic probe adapted for transmitting and receiving ultrasonic waves, and for practicing an analog signal processing on received signals obtained through said ultrasonic probe;

an input unit for inputting a control signal to control said analog unit; and an output unit for outputting the signals generated from said analog unit to an exterior, wherein all of said units are incorporated in one united body;

a first computer system connected to said input unit and said output unit of said ultrasonic module, said first computer system being capable of performing a transmission of a control signal for controlling said ultrasonic module, and also being capable of performing data communication, via a communication line, including a transmission of signals output from said ultrasonic module; and a second computer system connected via said communication line to said first computer system, said second computer system being capable of performing a data communication including a reception of the signals output from said ultrasonic module and transmitted from said first computer system, and also being capable of producing images based on received signals, wherein said second computer system includes:

transmitting means for transmitting to said first computer system a signal representative of a navigation image to support an operation for deriving images using said ultrasonic module, and wherein said first computer system includes:
  receiving means for receiving the signal representative of the navigation image transmitted from said second computer system; and
  navigation image display means for displaying the navigation image based on received signals.

33. An ultrasonic diagnostic system according to claim 32, wherein said ultrasonic diagnostic system comprises an ultrasonic probe device having an ultrasonic probe for transmitting and receiving ultrasonic waves, a pointing device for designating a position on a screen, and a cable for carrying a transmission of signals transferred between said ultrasonic probe and said pointing device and said ultrasonic module.

34. An ultrasonic diagnostic system according to claim 32, wherein said ultrasonic diagnostic system comprises an ultrasonic probe device having an ultrasonic probe for transmitting and receiving ultrasonic waves, a pointing device for designating a position on a screen, a first cable for carrying a transmission of signals transferred between said ultrasonic probe and said ultrasonic module, and a second cable for carrying a transmission of signals transferred between said pointing device and said first computer system.

35. An ultrasonic diagnostic system comprising:
  an ultrasonic module including:
    an analog unit for supplying drive signals for a transmission of ultrasonic waves to an to an ultrasonic probe adapted for transmitting and receiving ultrasonic waves, and for practicing an analog signal processing on received signals obtained through said ultrasonic probe;
    a digital unit for practicing a digital signal processing on signals generated from said analog unit;
    a display circuit unit for practicing a processing for causing an image display to display an image based on signals generated from said digital unit;
    a system control unit for controlling said analog unit, said digital unit, and said display circuit unit;
    an operation panel unit for inputting an instruction as to a control specification to said system control unit;
    an input unit for inputting a control specification issued from an exterior to said system control unit; and
    an output unit for outputting the signals generated from said digital unit to an exterior,
    wherein all said units are incorporated in one united body; and
  a computer system connected to said input unit and said output unit of said ultrasonic module, said computer system being capable of performing an output of a control specification for controlling said ultrasonic module, a filing of information based on signals generated from said output unit, and a display of images based on the signals generated from said output unit,
  wherein said ultrasonic diagnostic system includes said ultrasonic probe, a pointing device for designating a position on a screen, and a cable for carrying a transmission of signals transferred between said ultrasonic probe and said pointing device and said ultrasonic module.

36. An ultrasonic diagnostic system comprising:
  an ultrasonic module including:
    an analog unit for supplying signals for a transmission of ultrasonic waves to an to an ultrasonic probe adapted for transmitting and receiving ultrasonic waves, and for practicing an analog signal processing on received signals obtained through said ultrasonic probe;
    a system control unit for controlling said analog unit; and
    an output unit for outputting signals generated from said analog unit to an exterior,
    wherein all said units are incorporated in one united body; and
  a computer system connected to said output unit of said ultrasonic module, said computer system being capable of performing a digital signal processing to be practiced on signals generated from said ultrasonic module, a filing of information based on signals subjected to the digital signal processing, and a display of images based on the signals subjected to the digital signal processing,
  wherein said ultrasonic diagnostic system includes said ultrasonic probe, a pointing device for designating a position on a screen, and a cable for carrying a transmission of signals transferred between said ultrasonic probe and said pointing device and said ultrasonic module.

37. An ultrasonic diagnostic system comprising:
  an ultrasonic module including:
    an analog unit for supplying drive signals for a transmission of ultrasonic waves to an to an ultrasonic probe adapted for transmitting and receiving ultrasonic waves, and for practicing an analog signal processing on received signals obtained through said ultrasonic probe;
    a digital unit for practicing a digital signal processing on signals generated from said analog unit;
    a display circuit unit for practicing a processing for causing an image display to display an image based on signals generated from said digital unit;
    a system control unit for controlling said analog unit, said digital unit, and said display circuit unit;
    an operation panel unit for inputting an instruction as to a control specification to said system control unit;
    an input unit for inputting a control specification issued from an exterior to said system control unit; and
    an output unit for outputting the signals generated from said digital unit to an exterior,
    wherein all said units are incorporated in one united body; and
  a computer system connected to said input unit and said output unit of said ultrasonic module, said computer system being capable of performing an output of a control specification for controlling said ultrasonic module, a filing of information based on signals generated from said output unit, and a display of images based on the signals generated from said output unit,
  wherein said ultrasonic diagnostic system includes said ultrasonic probe, a pointing device for designating a position on a screen, a first cable for carrying a transmission of signals transferred between said ultrasonic probe and said ultrasonic module, and a second cable for carrying a transmission of signals between said pointing device and said computer system.

38. An ultrasonic diagnostic system comprising:
  an ultrasonic module including:
    an analog unit for supplying signals for a transmission of ultrasonic waves to an to an ultrasonic probe adapted for transmitting and receiving ultrasonic waves, and for practicing an analog signal processing on received signals obtained through said ultrasonic probe;
    a system control unit for controlling said analog unit; and
    an output unit for outputting signals generated from said analog unit to an exterior, wherein all said units are incorporated in one united body; and a computer system connected to said output unit of said ultrasonic module, said computer system being capable of performing a digital signal processing to be practiced on signals generated from said ultrasonic module, a filing of information based on signals subjected to the digital signal processing, and a display of images based on the signals subjected to the digital signal processing, wherein said ultrasonic diagnostic system includes said ultrasonic probe, a pointing device for designating a position on a screen, a first cable for carrying a transmission of signals transferred between said ultrasonic probe and said ultrasonic module, and a second cable for carrying a transmission of signals between said pointing device and said computer system.

* * * * *